(12) United States Patent
Abouabdellah et al.

(10) Patent No.: US 8,865,738 B2
(45) Date of Patent: Oct. 21, 2014

(54) 5-MEMBERED HETEROCYCLIC COMPOUND CYCLOPENTA [C]PYRROLYLALKYLCARBAMATE DERIVATIVES, PREPARATION THEREOF, AND THERAPEUTIC USE THEREOF

(75) Inventors: Ahmed Abouabdellah, Paris (FR); Aude Fayol, Paris (FR); Alistair Lochead, Paris (FR); Mourad Saady, Paris (FR); Julien Vache, Paris (FR); Philippe Yaiche, Paris (FR)

(73) Assignee: Sanofi, Paris (FR)

( * ) Notice: Subject to any disclaimer, the term of this patent is extended or adjusted under 35 U.S.C. 154(b) by 183 days.

(21) Appl. No.: 13/319,635

(22) PCT Filed: May 11, 2010

(86) PCT No.: PCT/FR2010/050912
§ 371 (c)(1),
(2), (4) Date: Feb. 1, 2012

(87) PCT Pub. No.: WO2010/130943
PCT Pub. Date: Nov. 18, 2010

(65) Prior Publication Data
US 2012/0136026 A1 May 31, 2012

(30) Foreign Application Priority Data
May 12, 2009 (FR) .................... 09 02267

(51) Int. Cl.
*C07D 413/14* (2006.01)
*C07D 261/10* (2006.01)
*C07D 277/22* (2006.01)
*C07D 231/12* (2006.01)
*C07D 401/14* (2006.01)

(52) U.S. Cl.
CPC ............ *C07D 413/14* (2013.01); *C07D 261/10* (2013.01); *C07D 277/22* (2013.01); *C07D 231/12* (2013.01); *C07D 401/14* (2013.01)
USPC .......................................... 514/312; 546/159

(58) Field of Classification Search
USPC .......................................... 546/159; 514/312
See application file for complete search history.

(56) References Cited

U.S. PATENT DOCUMENTS 6,995,184 B2   2/2006   Barth et al.

FOREIGN PATENT DOCUMENTS

| WO | WO2005/070910 A2 | 8/2005 |
| WO | WO2005/090322 A1 | 9/2005 |
| WO | WO2005/090347 A1 | 9/2005 |

OTHER PUBLICATIONS

International Preliminary Report on Patentability dated Nov. 15, 2011 issued in PCT/FR2010/050912.
International Search Report dated Aug. 24, 2010 issued in PCT/FR2010/050912.
Smith, et al., "Anandamide induces cardiovascular and respiratory reflexes via vaso sensory nervesin the anaesthetized rat"; British Journal of Pharmacology 2001, 134, 655-663.
De Petrocellis, et al., "Endocannabinoids and fatty acid amides in cancer, inflammation and related disorders"; Chemistry and Physics of Lipids, (2000), 108, 191-209.
Ueda, et al., The fatty acid amide hydrolase (FAAH); Chemistry and Physics of Lipids, (2000), 108, 107-121.
Izzo, et al., "The gastrointestinal pharmacology of annabinoids"; Current Opinion in Pharmacology 2001, 2, 597-603.
Salzet, et al., "Comparitive biology of the endocannabinoid system"; European Journal of Biochemistry 2000, 267, 4917-4927.
Van Sickle, et al., "Cannabinoids Inhibit Emesis Through CB1 Receptors in the Brainstem of the Ferret"; Gastroenterology 2001, 121, 767-774.
Martin, et al.; "Cannabinoid Transmission and Pain Perception"; Neurobiology of Disease 1998, 5, 447-461.
Consroe, et al., "Brain Cannabinoid Systems as Targets for the Therapy of Neurological Disorders"; Neurobiology of Disease 1998, 5, 534-551.
Jagger, et al., "The anti-hyperalgesic actions of the cannabinoid anandamide and the putative CB2 receptor agonist palmitoylethanolamidein visceral and somatic inflammatory pain"; Pain 1998, 76, 189-199.
Porter, et al., "The endocannabinoid nervous system: unique opportunities for therapetuic intervention"; Pharmacology and Therapeutics 2001, 90, 45-60.
Carley, et al., "Functional Role for Cannabinoids in Respiratory Stability During Sleep"; Sleep 2002, 25, 391-398.
Piomelli, et al., "The endocannabinoid system as a target for therapeutic drugs"; Trends in Pharmacological Sciences 2000, 21, 218-224.
Mendelson, et al., "The Hypnotic Actions of the Fatty Acid Amide, Oleamide", Neuropsychopharmacology 2001, vol. 25, No. S5 S36-S39.

(Continued)

Primary Examiner — D M Seaman
(74) Attorney, Agent, or Firm — Scully, Scott, Murphy & Presser P.C.

(57) ABSTRACT

The invention relates to compounds of the general formula (I) where: $R_2$ is a hydrogen or fluorine atom or a hydroxyl, cyano, trifluoromethyl, $C_{1-6}$-alkyl, $C_{1-6}$-alkoxy, or $NR_8R_9$ group; m and p have a value of 1; n and o have the same value which is 0 or 1; A is a covalent bond or a $C_{1-8}$-alkylene group; $R_1$ is an optionally substituted aryl or heteroaryl group; $R_3$ is a hydrogen or fluorine atom or a $C_{1-6}$-alkyl group or a trifluoromethyl group; $R_4$ is an optionally substituted 5-membered heterocyclic compound; wherein the compounds can be in the state of a base or an acid addition salt. The present invention can be used in therapeutics.

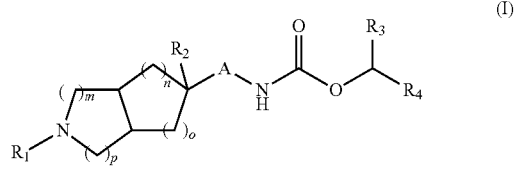

(I)

15 Claims, No Drawings

(56) References Cited

OTHER PUBLICATIONS

Hillard, et al., "Endocannabinoids and Vascular Function"; The Journal of Pharmacology and Experimental Therapeutics, vol. 294, 2000, 27-32.

Baker, et al., "Endocannabinoids control spasticity in a multiple sclerosis model"; The FASEB Journal 2001, 15, 300-302.

Murillo-Rodriquez, et al., "Anandamide-induced sleep is blocked by SRI41716A, a CBI receptor antagonist and by U73122, a phospholipase C inhibitor"; Neuropharmacology and Neurotoxicology, vol. 12, No. 10, Jul. 2001, 2131-2136.

Szallasi, et al., "Vaniolloid Receptor Ligands, Hopes and Realities for the Future", Drugs & Aging 2001: 18 (8): 561-573.

5-MEMBERED HETEROCYCLIC COMPOUND CYCLOPENTA[C]PYRROLYLALKYLCARBAMATE DERIVATIVES, PREPARATION THEREOF, AND THERAPEUTIC USE THEREOF

The invention relates to cyclopenta[c]pyrrolylalkylcarbamate derivatives of 5-membered heterocycles, to their preparation and to their therapeutic use.

There is still a need to find and develop products that inhibit the enzyme FAAH (Fatty Acid Amide Hydrolase). The compounds of the invention satisfy this aim.

The compounds of the invention correspond to the general formula (I):

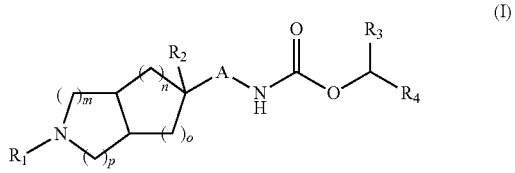

in which
$R_2$ represents a hydrogen or fluorine atom or a hydroxyl, cyano, trifluoromethyl, $C_{1-6}$-alkyl, $C_{1-6}$-alkoxy or $NR_8R_9$ group;
m and p have the value 1;
n and o have the same value and have the value 0 or 1;
A represents a covalent bond or a group $C_{1-8}$-alkylene;
$R_1$ represents a group $R_5$ optionally substituted with one or more groups $R_6$ and/or $R_7$;
  $R_5$ represents a group chosen from phenyl, pyridyl, pyridazinyl, pyrimidinyl, pyrazinyl, triazinyl, naphthalenyl, quinolinyl, isoquinolinyl, phthalazinyl, quinazolinyl, quinoxalinyl, cinnolinyl and naphthyridinyl;
  $R_6$ represents a halogen atom or a cyano, —$CH_2CN$, nitro, hydroxyl, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O— group;
  $R_7$ represents a group chosen from furyl, pyrrolyl, thienyl, oxazolyl, isoxazolyl, thiazolyl, isothiazolyl, imidazolyl, pyrazolyl, phenyl, pyridyl, pyridazinyl, pyrimidinyl, pyrazinyl and triazinyl; the group(s) $R_7$ possibly being substituted with one or more groups $R_6$ that may be identical to or different from each other;
$R_3$ represents a hydrogen or fluorine atom, a group $C_{1-6}$-alkyl or a trifluoromethyl group;
$R_4$ represents a 5-membered heterocycle chosen from furyl, pyrrolyl, thienyl, thiazolyl, isothiazolyl, oxazolyl, isoxazolyl, pyrazolyl, oxadiazolyl, thiadiazolyl, imidazole, triazolyl and tetrazolyl;
this heterocycle being optionally substituted with one or more substituents chosen from a halogen atom, a $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)(C_{1-3}$-alkylene-$NR_{10}R_{11})$, $SO_2R_8$, $SO_2NR_8R_9$ or —O—($C_{1-3}$-alkylene)-O— group;
$R_8$ and $R_9$ represent, independently of each other, a hydrogen atom or a $C_1$-$C_6$-alkyl group, or form, with the atom(s) that bear(s) them,
in the case of $NR_8R_9$, a ring chosen from azetidine, pyrrolidine, piperidine, morpholine, thiomorpholine, azepine, oxazepine and piperazine rings, this ring being optionally substituted with a $C_1$-$C_6$-alkyl or benzyl group;
in the case of $NR_8COR_9$, a lactam ring; in the case of $NR_8CO_2R_9$, an oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring;
$R_{10}$ and $R_{11}$ represent, independently of each other, a hydrogen atom or a $C_{1-6}$-alkyl group.

Among the compounds of general formula (I), a first subgroup of compounds is formed from the compounds for which $R_2$ represents a hydrogen atom or a fluorine atom. Among the compounds of general formula (I), a second subgroup of compounds is formed from the compounds for which $R_2$ represents a hydrogen atom. Among the compounds of general formula (I), a third subgroup of compounds is formed from the compounds for which $R_2$ represents a fluorine atom.

Among the compounds of general formula (I), a fourth subgroup of compounds is formed from the compounds for which m, n, o and p have the value 1. Among the compounds of general formula (I), a fifth subgroup is formed from the compounds for which m and p have the value 1, and, n and o have the value 0.

Among the compounds of general formula (I), a sixth subgroup of compounds is formed from the compounds for which A represents a covalent bond, a methylene or an ethylene. Among the compounds of general formula (I), a seventh subgroup of compounds is formed from the compounds for which A represents a covalent bond.

Among the compounds of general formula (I), an eighth subgroup of compounds is formed from the compounds for which A represents a methylene. Among the compounds of general formula (I), a ninth subgroup of compounds is formed from the compounds for which A represents an ethylene.

Among the compounds of general formula (I), a tenth subgroup of compounds is formed from the compounds for which $R_1$ represents a group $R_5$ which is unsubstituted or is substituted with one or more groups $R_6$ and/or $R_7$;
  $R_5$ represents a pyridyl or quinolinyl group;
  $R_6$ represents a halogen atom, more particularly a fluorine or bromine atom, or a $C_{1-6}$-haloalkyl group, more particularly a trifluoromethyl group or a $C_{1-6}$-alkyl group, more particularly a methyl group;
  $R_7$ represents a group chosen from pyrazolyl, pyridyl and phenyl, the latter groups possibly being substituted with one or more groups $R_6$ that may be identical to or different from each other.

Among the compounds of general formula (I), an eleventh subgroup of compounds is formed from the compounds for which $R_1$ represents a group $R_5$ substituted with one or more groups $R_6$ and/or $R_7$;
  $R_5$ represents a pyridyl group, more particularly a pyrid-2-yl group;
  $R_6$ represents a halogen atom, more particularly a fluorine or bromine atom, or a $C_{1-6}$-haloalkyl group, more particularly a trifluoromethyl group or a $C_{1-6}$-alkyl group, more particularly a methyl group;
  $R_7$ represents a group chosen from pyrazolyl, pyridyl and phenyl, the latter groups possibly being substituted with one or more groups $R_6$ that may be identical to or different from each other.

Among the compounds of general formula (I), a twelfth subgroup of compounds is formed from the compounds for which $R_1$ represents a group $R_5$ substituted with one or more groups $R_6$;
$R_5$ represents a quinolinyl group, more particularly a quinolin-2-yl group;
$R_6$ represents a halogen atom, more particularly a fluorine atom.

Among the compounds of general formula (I), a thirteenth subgroup of compounds is formed from the compounds for which $R_3$ represents a hydrogen atom.

Among the compounds of general formula (I), a fourteenth subgroup of compounds is formed from the compounds for which $R_4$ represents a group chosen from a thiazolyl, a triazolyl, or an isoxazolyl;
this group being unsubstituted or substituted with one or more $C_{1-6}$-alkyl, $CO_2R_8$ or $CONR_8R_9$ groups;
$R_8$ and $R_9$ represent, independently of each other, a hydrogen atom or a $C_{1-6}$-alkyl group. More particularly, the $C_{1-6}$-alkyl group is a methyl or ethyl.

Among the compounds of general formula (I), a fifteenth subgroup of compounds is formed from the compounds for which $R_4$ represents a thiazol-4-yl group, this group being unsubstituted.

Among the compounds of general formula (I), a sixteenth subgroup of compounds is formed from the compounds for which $R_4$ represents an isoxazol-5-yl group;
this group being substituted with one or more $CO_2R_8$ or $CONR_8R_9$ groups;
$R_8$ and $R_9$ represent, independently of each other, a hydrogen atom or a $C_{1-6}$-alkyl group. More particularly, the $C_{1-6}$-alkyl group is a methyl or ethyl.

Among the compounds of general formula (I), a seventeenth subgroup of compounds is formed from the compounds for which $R_4$ represents a 1H-1,2,4-triazol-5-yl group; this group being substituted with one or more $C_{1-6}$-alkyl groups.

Among the compounds of general formula (I), an eighteenth subgroup of compounds is formed by the compounds of general formula (I) in which $R_1$ and/or $R_2$ and/or $R_3$ and/or $R_4$ and/or n and/or m and/or o and/or p and/or A are all as defined in the above groups.

Among the compounds of general formula (I), the following compounds may be mentioned (IUPAC nomenclature generated by the AutoNom software):
1. thiazol-4-ylmethyl ({(3aR,5s,6aS)-2-[6-(trifluoro-methyl)pyrid-2-yl]octahydrocyclopenta[c]pyrrol-5-yl}methyl) carbamate (exo)
2. thiazol-4-ylmethyl {[(3aR,5s,6aS)-2-(5-bromopyrid-2-yl) octahydrocyclopenta[c]pyrrol-5-yl]methyl}carbamate (exo)
3. thiazol-4-ylmethyl ({(3aR,5s,6aS)-2-[5-(4-fluoro-phenyl) pyrid-2-yl]octahydrocyclopenta[c]pyrrol-5-yl}-methyl) carbamate (exo)
4. thiazol-4-ylmethyl ({(3aR,5s,6aS)-2-[5-(1-methyl-1H-pyrazol-4-yl)pyrid-2-yl]octahydrocyclopenta[c]pyrrol-5-yl}methyl)carbamate (exo)
5. thiazol-4-ylmethyl {(3aR,5s,6aS)-2-[6-(trifluoro-methyl) pyrid-2-yl]octahydrocyclopenta[c]pyrrol-5-yl}-carbamate (exo)
6. thiazol-4-ylmethyl [(3aR,5s,6aS)-2-(6-fluoroquinolin-2-yl)octahydrocyclopenta[c]pyrrol-5-yl]carbamate (exo)
7. (1-methyl-1H-1,2,4-triazol-5-yl)methyl ({(3aR,5s,6aS)-2-[5-(4-fluorophenyl)pyrid-2-yl]octahydrocyclopenta[c]-pyrrol-5-yl}methyl)carbamate (exo)
8. (1-methyl-1H-1,2,4-triazol-5-yl)methyl {[(3aR,5s,6aS)-2-(5'-fluoro-2,3'-bipyrid-6-yl)octahydrocyclopenta[c]-pyrrol-5-yl]methyl}carbamate (exo)
9. (3-carbamoylisoxazol-5-yl)methyl ({(3aR,5s,6aS)-2-[5-(4-fluorophenyl)pyrid-2-yl]octahydrocyclopenta[c]pyrrol-5-yl}methyl)carbamate (exo)
10. [3-(methylcarbamoyl)isoxazol-5-yl]methyl {2-[(3aR,5r, 6aS)-2-(5-bromopyrid-2-yl)octahydrocyclopenta[c]-pyrrol-5-yl]ethyl}carbamate (endo)
11. (3-carbamoylisoxazol-5-yl)methyl {2-[(3aR,5r,6aS)-2-(5-bromopyrid-2-yl)octahydrocyclopenta[c]pyrrol-5-yl] ethyl}-carbamate (endo)
12. (3-carbamoylisoxazol-5-yl)methyl {[(3aR,5r,6aS)-5-fluoro-2-(6-fluoroquinolin-2-yl)octahydrocyclopenta[c]-pyrrol-5-yl]methyl}carbamate (exo)
13. [3-(methylcarbamoyl)isoxazol-5-yl]methyl {[(3aR,5s, 6aS)-2-(6-fluoroquinolin-2-yl)octahydrocyclo-penta[c] pyrrol-5-yl]methyl}carbamate (exo)
14. [3-(methylcarbamoyl)isoxazol-5-yl]methyl [3-(6-fluoro-quinolin-2-yl)-3-azabicyclo[3.1.0]hex-6-yl]carbamate
15. ethyl 5-{[({3-[5-(4-fluorophenyl)pyrid-2-yl]-3-aza-bicyclo[3.1.0]hex-6-yl}carbamoyl)oxy]methyl}isoxazole-3-carboxylate
16. (3-carbamoylisoxazol-5-yl)methyl [3-(6-fluoroquinolin-2-yl)-3-azabicyclo[3.1.0]hex-6-yl]carbamate
17. (3-carbamoylisoxazol-5-yl)methyl {3-[5-(4-fluoro-phenyl)pyrid-2-yl]-3-azabicyclo[3.1.0]hex-6-yl}carbamate
18. [3-(methylcarbamoyl)isoxazol-5-yl]methyl {3-[5-(4-fluorophenyl)pyrid-2-yl]-3-azabicyclo[3.1.0]hex-6-yl}-carbamate
19. [3-(dimethylcarbamoyl)isoxazol-5-yl]methyl {3-[5-(4-fluorophenyl)pyrid-2-yl]-3-azabicyclo[3.1.0]hex-6-yl}-carbamate The compounds of general formula (I) may comprise one or more asymmetric carbons. They may exist in the form of enantiomers or diastereoisomers. The compounds of general formula (I) may also exist in the form of cis or trans stereoisomers. These stereoisomers, enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

In the context of the invention, the following definitions apply:
$C_{t-z}$ in which t and z may take values from 1 to 8, a carbon-based chain possibly containing from t to z carbon atoms, for example $C_{1-3}$ is a carbon-based chain that may contain from 1 to 3 carbon atoms;
alkyl, a linear or branched, saturated aliphatic group; for example, a $C_{1-6}$-alkyl group represents a linear or branched carbon-based chain of 1 to 6 carbon atoms, more particularly a methyl, ethyl, propyl, isopropyl, butyl, isobutyl, tert-butyl, pentyl or hexyl;
alkylene, a linear or branched, saturated divalent alkyl group, for example a $C_{1-3}$-alkylene group represents a linear or branched divalent carbon-based chain of 1 to 3 carbon atoms, more particularly a methylene, ethylene, 1-methylethylene or propylene;
cycloalkyl, a cyclic alkyl group, for example a $C_{3-7}$-cycloalkyl group represents a cyclic carbon-based group of 3 to 7 carbon atoms, more particularly a cyclopropyl, cyclobutyl, cyclopentyl, cyclohexyl or cycloheptyl;
alkoxy, an —O-alkyl group containing a linear or branched, saturated aliphatic chain;
thioalkyl, an —S-alkyl group containing a linear or branched, saturated aliphatic chain;
haloalkyl, an alkyl group in which one or more hydrogen atoms have been replaced with a halogen atom;

haloalkoxy, an alkoxy group in which one or more hydrogen atoms have been replaced with a halogen atom;

halothioalkyl, a thioalkyl group in which one or more hydrogen atoms have been replaced with a halogen atom;

halogen atom, a fluorine, a chlorine, a bromine or an iodine.

The term 'exo' corresponds to the group —R2 in the trans position relative to the ring junction hydrogens. The term 'endo' corresponds to the group —R2 in the cis position relative to the ring junction hydrogens.

r and s indicate the stereochemistry of the pseudo-asymmetric carbon atoms, according to IUPAC rules.

The compounds of the invention may be prepared according to various methods, illustrated by the schemes that follow. These methods, and also the intermediate compounds used, are a subject of the present invention.

base such as triethylamine, pyridine, N,N-dimethylaminopyridine or diisopropylethylamine in a solvent such as toluene or dichloroethane, at a temperature between room temperature and the reflux temperature of the solvent.

One variant for obtaining the compounds of general formula (I) (scheme 1) consists in reacting an amine of general formula (II), as defined above, with phenyl or 4-nitrophenyl chloroformate, in the presence of a base such as triethylamine or diisopropylethylamine, in a solvent such as dichloromethane or tetrahydrofuran, at a temperature between 0° C. and room temperature, to give the carbamate derivative of general formula (IV), in which A, $R_1$, $R_2$, m, n, o and p are as defined in the general formula (I) defined above, and Z represents a hydrogen atom or a nitro group. The carbamate derivative of general formula (IV) thus obtained is then converted into a compound of general formula (I), via the action

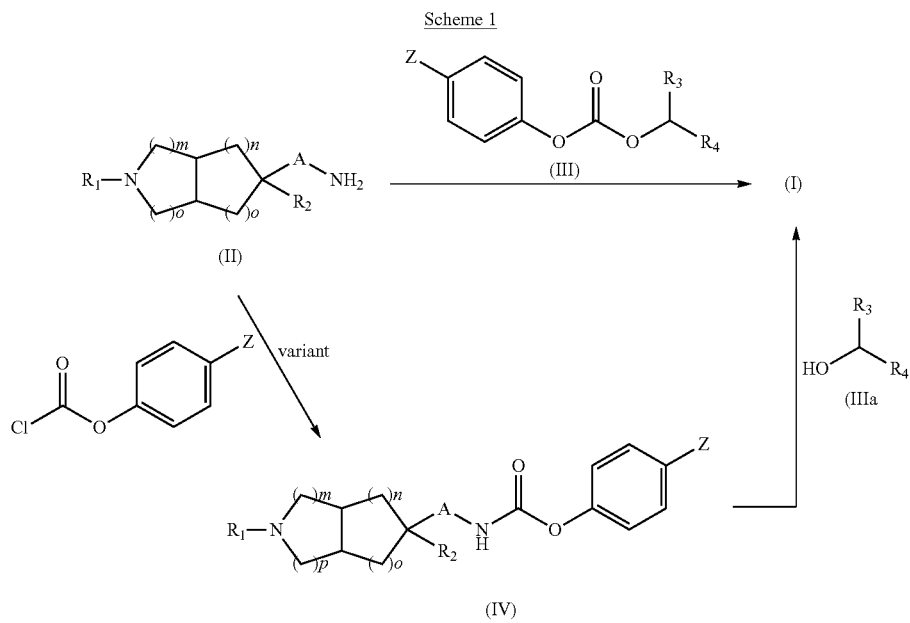

Thus, a first method (scheme 1) consists in reacting an amine of general formula (II), in which A, $R_1$, $R_2$, m, n, o and p are as defined in the general formula (I) defined above, with a carbonate of general formula (III) in which Z represents a hydrogen atom or a nitro group, and $R_3$ and $R_4$ are as defined in the general formula (I) defined above, in the presence of a base such as triethylamine, pyridine, N,N-dimethylaminopyridine or diisopropylethylamine, in a solvent such as toluene or dichloroethane, at a temperature between room temperature and the reflux temperature of the solvent.

of an alcohol of general formula $HOCHR_3R_4$ (IIIa), as defined above, in the presence of a base such as triethylamine, pyridine, N,N-dimethylaminopyridine or diisopropylethylamine, in a solvent such as toluene or dichloroethane, at a temperature between room temperature and the reflux temperature of the solvent.

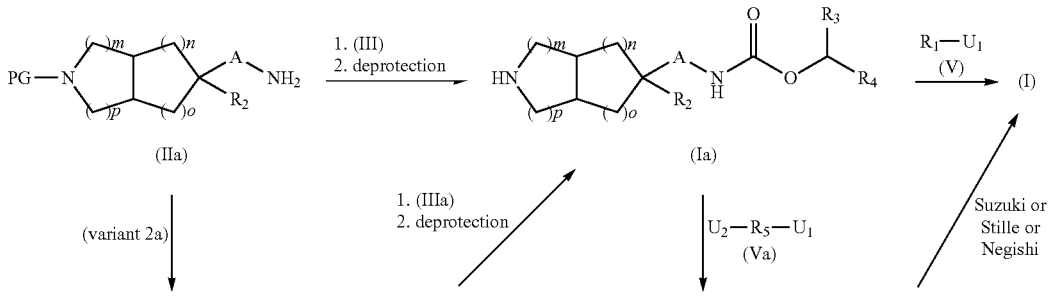

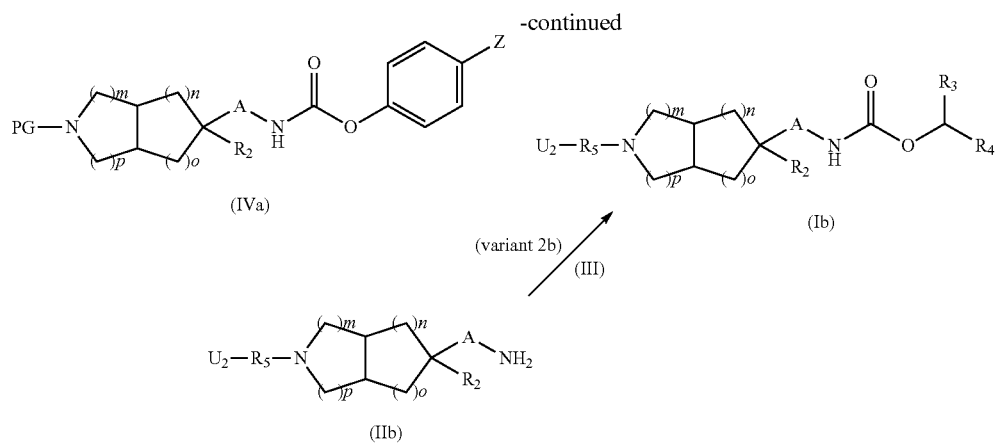

A second method (Scheme 2) consists in reacting, in a first stage, an amine of general formula (IIa), in which A, $R_2$, m, n, o and p are as defined in the general formula (I) defined above, and PG represents a protecting group such as a Boc (tert-butyloxycarbonyl), a Cbz (benzyloxycarbonyl), a benzyl or a benzhydryl, with a carbonate of general formula (III) as defined above, under the conditions described above during the reaction of the amine of general formula (II) with the carbonate of general formula (III), followed by a deprotection reaction, for example in the presence of a solution of hydrochloric acid (5N) in isopropanol or dioxane, to obtain the intermediate of general formula (Ia), in which A, $R_2$, $R_3$, $R_4$, m, n, o and p are as defined in the general formula (I).

One variant for obtaining the intermediates of general formula (Ia) (Scheme 2-variant 2a) consists in reacting an amine of general formula (IIa), as defined above, with phenyl or 4-nitrophenyl chloroformate, in the presence of a base such as triethylamine or diisopropylethylamine, in a solvent such as dichloromethane or tetrahydrofuran, at a temperature of between 0° C. and room temperature, to give the carbamate derivative of general formula (IVa), in which A, $R_2$, m, n, o and p are as defined in the general formula (I) defined above, PG is as defined above and Z represents a hydrogen atom or a nitro group. The carbamate derivative of general formula (IVa) thus obtained is then converted into a compound of general formula (Ia), via the action of an alcohol of general formula HOCHR$_3$R$_4$ (IIIa), as defined above, in the presence of a base such as triethylamine, pyridine, N,N-dimethylaminopyridine or diisopropyl-ethylamine, in a solvent such as toluene or dichloroethane, at a temperature of between room temperature and the reflux temperature of the solvent, followed by a deprotection reaction, for example in the presence of a solution of hydrochloric acid (5N) in isopropanol or dioxane.

The compound of general formula (I) is then obtained by reaction of the compound of general formula (Ia) with a derivative of general formula (V), in which $R_1$ is as defined in the general formula (I) and $U_1$ represents a halogen atom or a triflate group, using aromatic or heteroaromatic nucleophilic substitution reaction conditions, for example by means of a base such as triethylamine, diisopropyl-ethylamine, pyridine or N,N-dimethylaminopyridine in a solvent such as dichloromethane, dichloroethane, acetonitrile, N,N-dimethylformamide, dioxane or tetrahydro-furan, at a temperature between 0° C. and the reflux temperature of the solvent. This conversion may also be performed using the Buchwald N-arylation or N-heteroarylation conditions, for example by means of a palladium or copper catalyst.

According to Scheme 2, the compounds of general formula (I), in which $R_1$ represents a group $R_5$ substituted especially with a group $R_6$ of the $C_{1-6}$-alkyl, $C_{3-7}$-cycloalkyl or $C_{3-7}$-cycloalkyl-$C_{1-3}$-alkylene type, or with a group $R_7$ as defined in the general formula (I) defined above, may also be prepared according to a coupling reaction, catalysed by means of a transition metal, for example palladium (0), performed on the compound of general formula (Ib), in which A, $R_2$, $R_3$, $R_4$, $R_5$, m, n, o and p are as defined in the general formula (I) and $U_2$ represents a chlorine, bromine or iodine atom or a triflate group, $U_2$ being in the position in which it is desired to introduce the group $R_6$ or $R_7$ (Scheme 2):
either via a reaction of Suzuki type, for example using an alkyl, cycloalkyl, aryl or heteroaryl boronic acid,
or according to a reaction of Stille type, for example using an aryl or heteroaryl trialkylstannous derivative,
or via a reaction of Negishi type, for example using an alkyl, cycloalkyl, aryl or heteroaryl halide zincate derivative.

The intermediate of general formula (Ib) as defined above is obtained beforehand by reacting an amine of general formula (Ia) as defined above with a derivative of general formula (Va), in which $R_5$, $U_1$ and $U_2$ are as defined above, using aromatic or heteroaromatic nucleophilic substitution reactions or Buchwald N-arylation or N-heteroarylation reactions, for example using a palladium or copper catalyst.

One variant for obtaining the intermediates of general formula (Ib) (Scheme 2-variant 2b) consists in reacting, in a first stage, an amine of general formula (IIb), in which A, $R_5$, $R_2$, m, n, o and p are as defined in the general formula (I) defined above, and $U_2$ is as defined above, with a carbonate of general formula (III) as defined above, under the conditions described above during the reaction of the amine of general formula (II) with the carbonate of general formula (III), to obtain the intermediate of general formula (Ib), in which A, $R_5$, $R_2$, $R_3$, $R_4$, m, n, o and p are as defined in the general formula (I), and $U_2$ is as defined above.

Another subject of the present invention relates to the compounds of general formula (Ia):

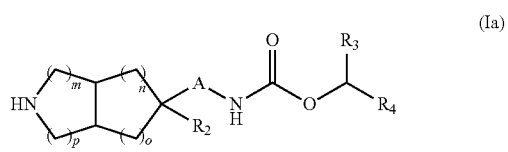

(Ia)

in which A, $R_2$, $R_3$, $R_4$, m, n, o and p are as defined in the general formula (I).

Among these compounds, mention may be made of:
thiazol-4-ylmethyl [(3aR,5s,6aS)-octahydrocyclopenta[c]-pyrrol-5-ylmethyl]carbamate;
thiazol-4-ylmethyl (3aR,5s,6aS)-octahydrocyclopenta[c]-pyrrol-5-ylcarbamate;
(1-methyl-1H-1,2,4-triazol-5-yl)methyl [(3aR,5s,6aS)-octahydrocyclopenta[c]pyrrol-5-ylmethyl]carbamate;
(3-carbamoylisoxazol-5-yl)methyl [(3aR,5s,6aS)-octahydro-cyclopenta[c]pyrrol-5-ylmethyl]carbamate;
ethyl 5-{[({2-[(3aR,5r,6aS)-octahydrocyclopenta[c]pyrrol-5-yl]ethyl}carbamoyl)oxy]methyl}isoxazole-3-carboxylate;
ethyl 5-{[({[(3aR,5r,6aS)-5-fluorooctahydrocyclopenta[c]-pyrrol-5-yl]methyl}carbamoyl)oxy]methyl}isoxazole-3-carboxylate; and
ethyl 5-{[(3-azabicyclo[3.1.0]hex-6-ylcarbamoyl)oxy]methyl}-isoxazole-3-carboxylate.

Another subject of the present invention relates to the compounds of general formula (II):

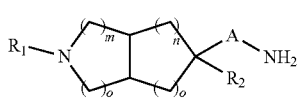

in which A, $R_1$, $R_2$, m, n, o and p are as defined in the general formula (I).

Another subject of the present invention relates to the compounds of general formula (IV):

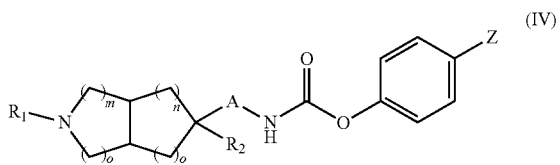

in which A, $R_1$, $R_2$, m, n, o and p are as defined in the general formula (I), and Z represents a hydrogen atom or a nitro group.

The other compounds of general formulae (II), (IIa), (IIb), (III), (IIIa), (V) and (Va) and also the other reactants are commercially available or described in the literature, or else may be prepared according to methods that are described therein or that are known to those skilled in the art.

The examples that follow illustrate the preparation of a number of compounds of the invention. These examples are not limiting, and serve merely to illustrate the invention. The microanalyses and the IR, NMR and/or LC-MS (liquid chromatography coupled to mass spectroscopy) spectra confirm the structures and the purities of the compounds obtained. MP (° C.) represents the melting point in degrees Celsius. $R_f$ indicates the retention time obtained by TLC (thin-layer chromatography) analysis.

The numbers given in parentheses in the titles of the examples correspond to those of the first column of the tables hereinbelow.

The IUPAC (International Union of Pure and Applied Chemistry) nomenclature was used to name the compounds in the examples below.

EXAMPLE 1

Compound No. 2

Thiazol-4-ylmethyl {[(3aR,5s,6aS)-2-(5-bromopy-rid-2-yl)-octahydrocyclopenta[c]pyrrol-5-yl] methyl}carbamate (exo)

1.1. tert-Butyl (3aR,5s,6aS)-5-cyanohexahydrocyclo-penta[c]-pyrrole-2(1H)-carboxylate 2.3 g (7.53 mmol) of tert-butyl (3aR,5r,6aS)-5-[(methyl-sulfonyl)oxy]hexahydrocyclopenta[c]pyrrole-2(1H)-carboxylate (WO 2006/108059) are put into solution in 25 ml of dimethylsulphoxide then 3.69 g (75.31 mmol) of sodium cyanide are added. The mixture is stirred at 80° C. for 1 hour.

It is allowed to return to room temperature and diluted by adding water and ethyl acetate. The aqueous phase is extracted with ethyl acetate, then the combined organic phases are dried over sodium sulphate, filtered and the filtrate is evaporated to dryness. The residue thus obtained is purified by chromatography on silica gel, eluting with a 95/5 to 85/15 mixture of cyclohexane and ethyl acetate. 0.81 g of product is obtained in the form of a white solid.

Melting point (° C.): 62-64° C.
$^1$H NMR (DMSO) δ (ppm): 3.48 (m, 2H), 3.19 (m, 1H), 3.00 (m, 2H), 2.78 (m, 2H), 1.99 (m, 2H), 1.88 (m, 2H), 1.39 (s, 9H).

1.2. tert-Butyl (3aR,5s,6aS)-5-(aminomethyl) hexahydrocyclo-penta[c]pyrrole-2(1H)-carboxylate 0.54 g (2.29 mmol) of tert-butyl (3aR,5s,6aS)-5-cyano-hexahydrocyclopenta[c]pyrrole-2(1H)-carboxylate, obtained in step 1.1., is put into solution in 20 ml of a 1M solution of sodium hydroxide in ethanol in the presence of a catalytic amount of Raney nickel (50% in water). The solution is stirred at room temperature under a hydrogen pressure of 4 bar using a Parr apparatus for 6 hours. After evaporating the ethanol, the solution is taken up in water and dichloromethane. The aqueous phase is extracted several times with dichloromethane. The combined organic phases are then washed with a saturated aqueous solution of sodium chloride then dried over sodium sulphate. After filtration and evaporation to dryness, 0.550 g of a colourless oil is obtained.

LC-MS: M+H=241
$^1$H NMR (DMSO) δ (ppm): 3.45 (m, 2H), 2.98 (m, 2H), 2.64 (m, 2H), 2.45 (d, 2H), 2.03 (m, 1H), 1.54 (m, 2H), 1.44 (m, 2H), 1.40 (s, 9H).

1.3. tert-Butyl (3aR,5s,6aS)-5-({[(1,3-thiazol-4-yl-methoxy)-carbonyl]amino}methyl)hexahydrocyclo-penta[c]pyrrole-2(1H)-carboxylate 0.550 g (2.29 mmol) of tert-butyl (3aR,5s,6aS)-5-(amino-methyl) hexahydrocyclopenta[c]pyrrole-2(1H)-carboxylate, obtained in step 1.2., 0.028 g (0.23 mmol) of N,N-dimethyl-4-aminopyridine, 1.20 ml (6.87 mmol) of N,N-diisopropyl-ethylamine and 0.705 g (2.52 mmol) of thiazol-4-ylmethyl 4-nitrophenylcarbonate (WO 2008/013834) are put into solution in 20 ml of 1,2-dichloroethane. The mixture is stirred at 70° C. for 1 hour and 30 minutes.

After returning to room temperature, water is added to the reaction medium. After extracting the aqueous phase with dichloromethane, the organic phases are successively washed three times with a 1M aqueous solution of sodium hydroxide, then twice with a saturated aqueous solution of ammonium chloride. After having dried the organic phases over sodium sulphate, they are filtered and the filtrate is evaporated to dryness. Thus, 1 g of crude product is obtained, which is used as is in the following step.

1.4. Thiazol-4-ylmethyl [(3aR,5s,6aS)-octahydrocyclopenta-[c]pyrrol-5-ylmethyl]carbamate 0.905 g (2.29 mmol) of tert-butyl (3aR,5s,6aS)-5-({[(thiazol-4-ylmethoxy)carbonyl]amino}methyl)hexahydrocyclopenta[c]-pyrrole-2(1H)-carboxylate, obtained in step 1.3., is put into solution in 20 ml of dichloromethane then 1.93 ml (22.90 mmol) of trifluoroacetic acid are added. The mixture is stirred at room temperature for 3 hours.

A treatment with 1M sodium hydroxide, after extraction with dichloromethane then drying over sodium sulphate and evaporating to dryness, resulted in 0.66 g of an orange oil.

LC-MS: M+H=282

$^1$H NMR (DMSO) δ (ppm): 8.95 (s, 1H), 7.48 (s, 1H), 7.10 (broad s, 1H), 4.92 (s, 2H), 2.80 (m, 4H), 2.33 (m, 2H), 2.20 (m, 2H), 1.98 (m, 1H), 1.23 (m, 4H).

1.5. Thiazol-4-ylmethyl{[(3aR,5s,6aS)-2-(5-bromopyrid-2-yl)octahydrocyclopenta[c]pyrrol-5-yl]methyl}carbamate 0.40 g (1.42 mmol) of thiazol-4-ylmethyl[(3aR,5s,6aS)-octa-hydrocyclopenta[c]pyrrol-5-ylmethyl]carbamate, obtained in step 1.4., is put into solution in 4 ml of acetonitrile in a sealed tube. 0.27 g (1.56 mmol) of 5-bromo-2-fluoropyridine and 0.5 ml of N,N-diisopropylethylamine are added. The mixture is stirred at 100° C. for 6 hours.

After returning to room temperature, water and ethyl acetate are added. The aqueous phase is extracted several times with ethyl acetate. The combined organic phases are washed with a saturated aqueous solution of ammonium chloride then dried over sodium sulphate. Purification on a silica gel column while eluting with a 99/1 then 96/4 mixture of dichloromethane and methanol made it possible to obtain 0.30 g of product in the form of a beige solid.

Melting point (° C.): 114-116° C.

LC-MS: M+H=437

$^1$H NMR (DMSO) δ (ppm): 9.10 (s, 1H), 8.12 (s, 1H), 7.65 (m, 2H), 7.30 (broad s, 1H), 6.48 (d, 1H), 5.12 (s, 2H), 3.53 (m, 2H), 3.15 (m, 2H), 2.96 (m, 2H), 2.82 (m, 2H), 2.21 (m, 1H), 1.58 (m, 4H).

EXAMPLE 2

Compound No. 3

Thiazol-4-ylmethyl ({(3aR,5s,6aS)-2-[5-(4-fluorophenyl)-pyrid-2-yl]octahydrocyclopenta[c]pyrrol-5-yl}methyl)-carbamate (exo)

Under an inert atmosphere, the following are introduced: 0.125 g (0.29 mmol) of thiazol-4-ylmethyl {[(3aR,5s,6aS)-2-(5-bromopyrid-2-yl)octahydrocyclopenta[c]pyrrol-5-yl]-methyl}carbamate, prepared in Example 1, step 1.5, 0.048 g (0.34 mmol) of 4-fluorophenylboronic acid, 0.279 g (0.86 mmol) of caesium carbonate in suspension in 2.5 ml of a 9/1 mixture of tetrahydrofuran and water. Added next is 0.023 g (0.03 mmol) of PdCl$_2$dppf.CH$_2$Cl$_2$. The mixture is then heated at around 75° C. for 2 hours and 30 minutes.

It is allowed to return to room temperature, then the filtrate is taken up with ethyl acetate and water, the aqueous phase is separated and extracted twice with ethyl acetate, the combined organic phases are washed with a saturated aqueous solution of sodium chloride and dried over sodium sulphate. After evaporating the solvent, the residue obtained is purified by preparative thin layer chromatography, eluting with ethyl acetate. 0.07 g of a beige solid is obtained.

Melting point (° C.): 129-131° C.

LC-MS: M+H=453

$^1$H NMR (DMSO) δ (ppm): 9.10 (s, 1H), 8.38 (s, 1H), 7.80 (d, 1H), 7.61 (m, 3H), 7.32 (broad s, 1H), 7.21 (m, 2H), 6.58 (d, 1H), 5.11 (s, 2H), 3.60 (m, 2H), 3.12 (m, 2H), 2.99 (m, 2H), 2.81 (m, 2H), 2.21 (m, 1H), 1.56 (m, 4H).

EXAMPLE 3

Compound No. 5

Thiazol-4-ylmethyl{(3aR,5s,6aS)-2-[6-(trifluoromethyl)pyrid-2-yl]octahydrocyclopenta[c]pyrrol-5-yl}carbamate (exo)

3.1. tert-Butyl (3aR,5s,6aS)-5-aminohexahydrocyclopenta[c]-pyrrole-2(1H)-carboxylate 1.0 g (3.27 mmol) of tert-butyl (3aR,5r,6aS)-5-[(methylsulfonyl)oxy]hexahydrocyclopenta[c]pyrrole-2(1H)-carboxylate (WO 2006/108059) is put into solution in 25 ml of N,N-dimethylformamide then 0.29 g (4.46 mmol) of sodium azide is added. The mixture is then stirred at 90° C. for 2 hours and minutes.

It is allowed to return to room temperature and diluted by adding water and ethyl acetate. The aqueous phase is extracted with ethyl acetate, then the combined organic phases are dried over sodium sulphate, filtered and the filtrate is evaporated to dryness. The residue obtained is used as is in the following step.

The compound tert-butyl (3aR,5s,6aS)-5-azidohexahydro-cyclo-penta[c]pyrrole-2(1H)-carboxylate, obtained previously, is put into solution in 15 ml of ethanol with 0.34 g (1.63 mmol) of Lindlar catalyst in a Parr apparatus under a pressure of 20 psi hydrogen at room temperature for 3 hours. After filtrating over celite and evaporating to dryness, tert-butyl (3aR,5s,6aS)-5-aminohexahydrocyclopenta[c]pyrrole-2 (1H)-carboxylate is obtained in the form of oil that is used as is in the following step.

LC-MS: M+H=227

$^1$H NMR (DMSO) δ (ppm): 3.41 (m, 3H), 2.99 (m, 2H), 2.68 (m, 2H), 1.54 (m, 2H), 1.50 (m, 2H), 1.45 (s, 9H).

3.2. Thiazol-4-ylmethyl (3aR,5s,6aS)-octahydrocyclopenta[c]-pyrrol-5-ylcarbamate The procedure described in Example 1, step 1.3 is followed. Starting from 0.74 g (3.27 mmol) of tert-butyl (3aR, 5s,6aS)-5-aminohexahydrocyclopenta[c]pyrrole-2(1H)-carboxylate, obtained in step 3.1., 1.71 ml (9.81 mmol) of N,N-diiso-propylethylamine, 0.04 g (0.33 mmol) of N,N-dimethylamino-pyridine and 0.91 g (3.27 mmol) of thiazol-4-ylmethyl 4-nitrophenylcarbonate (WO 2008/013834), 1.5 g of crude product are obtained, which are used as is in the following step.

The product tert-butyl (3aR,5s,6aS)-5-{[(thiazol-4-ylmethoxy)carbonyl]amino}hexahydrocyclopenta[c]pyrrole-2 (H)-carboxylate, obtained previously, is put into solution in 30 ml of dichloromethane then 2.76 ml of trifluoroacetic acid are added. The mixture is stirred at room temperature for 15 hours.

After a basic treatment with a 1M aqueous solution of sodium hydroxide and extraction with dichloromethane, 0.690 g of thiazol-4-ylmethyl (3aR,5s,6aS)-octahydrocyclopenta-[c]pyrrol-5-ylcarbamate is obtained in the form of a white solid.

Melting point (° C.): 135-137° C.
LC-MS: M+H=268
$^1$H NMR (DMSO) δ (ppm): 9.14 (s, 1H), 7.70 (s, 1H), 7.25 (broad s, 1H), 5.14 (s, 2H), 3.95 (m, 1H), 2.95 (m, 2H), 2.55 (m, 2H), 2.48 (m, 2H), 1.60 (m, 4H).

3.3. Thiazol-4-ylmethyl {(3aR,5s,6aS)-2-[6-(trifluoro-methyl)pyrid-2-yl]octahydrocyclopenta[c]pyrrol-5-yl}-carbamate The procedure described in Example 1, step 1.5. is followed. Starting from 0.1 g (0.37 mmol) of thiazol-4-ylmethyl (3aR,5s,6aS)-octahydrocyclopenta[c]pyrrol-5-ylcarbamate, 0.2 ml (1.12 mmol) of N,N-diisopropylethylamine and 0.07 g (0.45 mmol) of 2-fluoro-6-trifluoromethylpyridine, and after silica gel preparative thin layer chromatography, eluting with ethyl acetate, 0.08 g of pure product is obtained in the form of a solid.

Melting point (° C.): 148-150° C.
LC-MS: M+H=413
$^1$H NMR (DMSO) δ (ppm): 9.11 (s, 1H), 7.70 (m, 2H), 7.40 (m, 1H), 7.01 (d, 1H), 6.78 (d, 1H), 5.12 (s, 2H), 4.00 (m, 1H), 3.58 (m, 2H), 3.28 (m, 2H), 2.90 (m, 2H), 1.78 (m, 4H).

EXAMPLE 4

Compound No. 8

(1-Methyl-1H-1,2,4-triazol-5-yl)methyl {[(3aR,5s,6aS)-2-(5'-fluoro-2,3'-bipyrid-6-yl)otahydroctahydrocyclopenta[c]pyrrol-5-yl]-methyl}carbamate (exo)

4.1 tert-Butyl (3aR,5s,6aS)-5-({[(4-nitrophenoxy)carbonyl]-amino}methyl)hexahydrocyclopenta[c]pyrrole-2(1H)-carboxylate Added to a solution of 1.24 g (5.16 mmol) of tert-butyl (3aR,5s,6aS)-5-(aminomethyl)hexahydrocyclopenta[c]pyrrole-2(1H)-carboxylate, obtained in Example 1, step 1.2., and of 1.80 ml (10.32 mmol) of N,N-diisopropylethylamine in 30 ml of 1,2-dichloroethane, is a solution of 1.14 g (5.68 mmol) of para-nitrophenyl chloroformate in 20 ml of 1,2-dichloroethane at around 0° C. The mixture is then stirred at room temperature for 15 hours.

A saturated aqueous solution of ammonium chloride is added to the reaction medium. The aqueous phase is extracted several times with dichloromethane. The organic phases are then washed with a saturated aqueous solution of ammonium chloride then dried over sodium sulphate. Purification on a silica gel column while eluting with a 99/1 then 90/10 mixture of cyclohexane and ethyl acetate made it possible to obtain 1.30 g of product in the form of a solid.

Melting point (° C.): 132-134° C.
$^1$H NMR (DMSO) δ (ppm): 8.26 (d, 2H), 8.06 (m, 1H), 7.40 (d, 2H), 3.44 (m, 2H), 3.01 (m, 4H), 2.67 (m, 2H), 2.25 (m, 1H), 1.58 (m, 4H), 1.38 (s, 9H).

4.2. 6-Bromo-5'-fluoro-[2,3']bipyridyl

Added to a solution of 2.00 g (8.44 mmol) of 2,6-dibromopyridine in 80 ml of a 4/1 mixture of toluene and ethanol, are 1.18 g (8.44 mmol) of 5-fluoropyridine-3-boronic acid, 0.48 g (0.42 mmol) of Pd(PPh$_3$)$_4$ and 25 ml of a 1M aqueous solution of sodium carbonate. The mixture is stirred at 90° C. for 2 hours.

It is allowed to return to room temperature, the aqueous phase is extracted several times with ethyl acetate. The combined organic phases are dried over sodium sulphate, filtered and evaporated to dryness. The residue thus obtained is purified on a silica gel column, eluting with a 99/1 to 97/3 mixture of dichloromethane and methanol. 0.80 g of product is thus obtained in the form of a white solid.

Melting point (° C.): 122-124° C.
LC-MS: M+H=253
$^1$H NMR (DMSO) δ (ppm): 9.10 (s, 1H), 8.72 (s, 1H), 8.30 (d, 1H), 8.20 (d, 1H), 7.92 (t, 1H), 7.75 (s, 1H).

4.3. (1-methyl-1H-1,2,4-triazol-5-yl)methyl {[(3aR,5s,6aS)-2-(5'-fluoro-2,3'-bipyrid-6-yl)octahydrocyclopenta[c]pyrrol-5-yl]methyl}carbamate Added to a solution of 0.084 g (0.74 mmol) of (2-methyl-2H-[1,2,4]triazol-3-yl)methanol in 5 ml of 1,2-dichloroethane are 0.26 ml (1.48 mmol) of N,N-diisopropylethylamine, 0.01 g (0.07 mmol) of N,N-dimethylaminopyridine and 0.30 g (0.74 mmol) of tert-butyl (3aR,5s,6aS)-5-({[(4-nitrophenoxy)-carbonyl]amino}methyl)hexahydrocyclopenta[c]pyrrole-2(1H)-carboxylate, obtained in step 4.1. The mixture is stirred at room temperature for 5 hours.

After adding water, the aqueous phase is extracted three times with dichloromethane. The combined organic phases are successively washed with a 1M aqueous solution of sodium hydroxide then with a saturated aqueous solution of ammonium chloride. The organic phase is dried over sodium sulphate, filtered and evaporated to dryness. Thus, 0.31 g of crude product is obtained, which is used as is in the following step.

0.28 g (0.74 mmol) of tert-butyl (3aR,5s,6aS)-5-[({[(1-methyl-1H-1,2,4-triazol-5-yl)methoxy]carbonyl}amino)methyl]-hexahydrocyclopenta[c]pyrrole-2(1H)-carboxylate, obtained previously, is put into solution in 5 ml of dichloromethane then 0.62 ml (7.40 mmol) of trifluoroacetic acid are added. The mixture is stirred at room temperature for 15 hours.

A treatment with 1M sodium hydroxide, after extraction with dichloromethane then drying over sodium sulphate and evaporating to dryness, resulted in 0.18 g of an orange oil, used as is in the following step according to the procedure described in Example 1, step 1.5.

Starting from 0.06 g (0.21 mmol) of (1-methyl-1H-1,2,4-triazol-5-yl)methyl[(3aR,5s,6aS)-octahydrocyclopenta[c]-pyrrol-5-ylmethyl]carbamate, obtained previously, 0.07 ml (0.43 mmol) of N,N-diisopropylethylamine and 0.05 g (0.21 mmol) of 6-bromo-5'-fluoro-[2,3']bipyridyl, obtained in step 4.2., 0.022 g of product is obtained in the form of a white solid.

Melting point (° C.): 136-138° C.
LC-MS: M+H=452
$^1$H NMR (DMSO) δ (ppm): 9.15 (s, 1H), 8.60 (s, 1H), 8.30 (m, 1H), 7.90 (s, 1H), 7.62 (m, 1H), 7.45 (broad s, 1H), 7.31 (m, 1H), 6.57 (d, 1H), 5.15 (s, 2H), 3.88 (s, 3H), 3.68 (m, 2H), 3.28 (m, 2H), 2.99 (m, 2H), 2.85 (m, 2H), 2.25 (m, 1H), 1.60 (m, 4H).

EXAMPLE 5

Compound No. 9

(3-Carbamoylisoxazol-5-yl)methyl ({(3aR,5s,6aS)-2-[5-(4-fluorophenyl)pyrid-2-yl]octahydrocyclopenta[c]pyrrol-5-yl}-methyl)carbamate (exo)

5.1. tert-Butyl (3aR,5s,6aS)-5-[({[(3-carbamoylisoxazol-5-yl)methoxy]carbonyl}amino)methyl]hexahydrocyclopenta[c]-pyrrole-2(1H)-carboxylate The procedure described in Example 4, step 4.3 is followed. Starting from 0.48 g (1.18 mmol) of tert-butyl (3aR,5s,6aS)-5-({[(4-nitrophenoxy)carbonyl]amino}methyl)hexahydro-cyclopenta[c]pyrrole-2(1H)-carboxylate, obtained in Example 4, step 4.1., 0.17 g (1.18 mmol) of 5-(hydroxymethyl)-3-isoxazolecarboxamide, 0.41 ml (2.37 mmol) of N,N-diisopropylethylamine and 0.01 g (0.12 mmol) of N,N-4-dimethylaminopyridine, and after recrystallization in diethyl ether, 0.24 g of product is obtained in the form of a white solid.
Melting point (° C.): 186-188° C.
LC-MS: M+H=409
$^1$H NMR (DMSO) δ (ppm): 8.11 (broad s, 1H), 7.82 (broad s, 1H), 7.48 (broad s, 1H), 6.75 (s, 1H), 5.20 (s, 2H), 3.42 (m, 2H), 2.98 (m, 4H), 2.64 (m, 2H), 2.18 (m, 1H), 1.48 (m, 4H), 1.38 (s, 9H).

5.2. 2-Fluoro-5-(4-fluoro-phenyl)pyridine

The procedure described in Example 4, step 4.2 is followed. Starting from 2.0 g (14.29 mmol) of 4-fluorobenzeneboronic acid, 5.21 g (14.29 mmol) of 5-bromo-2-fluoropyridine, 0.82 g (0.71 mmol) of Pd(PPh$_3$)$_4$ and 50 ml of a 1M aqueous solution of sodium carbonate, 2.30 g of product is obtained in the form of a white solid.
Melting point (° C.): 98-100° C.
LC-MS: M+H=192
$^1$H NMR (DMSO) δ (ppm): 8.55 (m, 1H), 8.28 (dd, 1H), 7.78 (m, 2H), 7.54 (m, 2H), 7.28 (dd, 1H).

5.3. (3-carbamoylisoxazol-5-yl)methyl ({(3aR,5s,6aS)-2-[5-(4-fluorophenyl)pyrid-2-yl]octahydrocyclopenta[c]pyrrol-5-yl}methyl)carbamate The procedure described in Example 4, step 4.3 is followed. Starting from 0.20 g (1.18 mmol) of tert-butyl (3aR,5s,6aS)-5-[({[(3-carbamoylisoxazol-5-yl)methoxy]carbonyl}amino)-methyl]hexahydrocyclopenta[c]pyrrole-2(1H)-carboxylate, obtained in step 5.1., and 0.41 ml (4.90 mmol) of trifluoroacetic acid, 0.27 g of (3-carbamoylisoxazol-5-yl)-methyl[(3aR,5s,6aS)-octahydrocyclopenta[c]pyrrol-5-yl-methyl]carbamate is obtained in trifluoroacetate form used as is in the following step according to the procedure described in Example 1, step 1.5.
Starting from 0.10 g (0.24 mmol) of (3-carbamoylisoxazol-5-yl)methyl[(3aR,5s,6aS)-octahydrocyclopenta[c]pyrrol-5-yl-methyl]carbamate, obtained previously, 0.16 ml (0.95 mmol) of N,N-diisopropylethylamine and 0.04 g (0.24 mmol) of 2-fluoro-5-(4-fluorophenyl)pyridine, obtained in step 5.2., and after silica gel preparative thin layer chromatography, eluting with a 90/10/1 mixture of dichloromethane/methanol/aqueous ammonia, 0.018 g of product is obtained in the form of a white solid.
Melting point (° C.): 208-210° C.
LC-MS: M+H=480
$^1$H NMR (DMSO) δ (ppm): 8.40 (s, 1H), 7.95 (broad s, 1H), 7.78 (d, 1H), 7.68 (broad s, 1H), 7.60 (m, 2H), 7.35 (broad s, 1H), 7.22 (m, 2H), 6.75 (s, 1H), 6.52 (d, 1H), 5.19 (s, 2H), 3.61 (m, 2H), 3.22 (m, 2H), 3.01 (m, 2H), 2.82 (m, 2H), 2.25 (m, 1H), 1.60 (m, 4H).

EXAMPLE 6

Compound No. 10

[3-(Methylcarbamoyl)isoxazol-5-yl]methyl{2-[(3aR,5r,6aS)-2-(5-bromopyrid-2-yl)octahydrocyclopenta[c]pyrrol-5-yl]ethyl}carbamate (endo)

6.1. tert-Butyl (3aR,5r,6aS)-5-(2-aminoethyl)hexahydrocyclo-penta[c]pyrrole-2(1H)-carboxylate 0.95 g (5.37 mmol) of diethyl cyanomethylphosphonate is put into solution in 6 ml of tetrahydrofuran then 0.21 g (5.37 mmol) of sodium hydride is added at room temperature. After stirring for 10 min, 1.1 g (4.88 mmol) of tert-butyl (3aR,6aS)-5-oxohexahydrocyclopenta[c]pyrrole-2(1H)-carboxylate (*Tetrahedron*, 1993, 49(23), 5047-54) in 9 ml of tetrahydrofuran are added. The mixture is stirred at room temperature for 2 hours.
After adding water, the product is extracted several times with ethyl acetate, then the combined organic phases are dried over sodium sulphate. After filtration and evaporation to dryness, tert-butyl (3aR,5Z,6aS)-5-(cyanomethylidene)-hexahydrocyclopenta[c]pyrrole-2(1H)-carboxylate is obtained, which is used as is in the following step.
1.24 g (4.88 mmol) of tert-butyl (3aR,5Z,6aS)-5-(cyanomethylidene)hexahydrocyclopenta[c]pyrrole-2(1H)-carboxylate, obtained previously, are put into solution in 50 ml of a 1M solution of sodium hydroxide in ethanol in the presence of a catalytic amount of Raney nickel, at 50% in water. It is then stirred at room temperature for 4 hours, under a hydrogen pressure of 4 bar using a Parr apparatus.
After filtering over celite and evaporating the ethanol, the residue obtained is taken up in water and dichloromethane. The product is extracted several times with dichloromethane. The combined organic phases are then washed using a saturated aqueous solution of sodium chloride, then dried over sodium sulphate. After filtration and evaporation to dryness, 1.0 g of tert-butyl (3aR,5r,6aS)-5-(2-aminoethyl)-hexahydrocyclopenta[c]pyrrole-2(1H)-carboxylate is obtained in the form of an orange oil, which is used as is in the following step.
MS: M$^+$=254
$^1$H NMR (DMSO) δ(ppm): 3.35 (m, 2H), 3.10 (m, 2H), 2.52 (m, 4H), 2.02 (m, 2H), 1.93 (m, 1H), 1.40 (m, 2H), 1.38 (s, 9H), 0.92 (m, 2H).

6.2. tert-Butyl (3aR,5r,6aS)-5-{2-[({[3-(ethoxycarbonyl)-isoxazol-5-yl]methoxy}carbonyl)amino]ethyl}hexahydrocyclo-penta[c]pyrrole-2(1H)-carboxylate Added slowly to a solution of 0.33 g (1.97 mmol) of ethyl 5-hydroxymethylisoxazole-3-carboxylate and 0.34 ml (1.97 mmol) of N,N-diisopropylethylamine in 10 ml of 1,2-dichloroethane, cooled to 0° C., is 0.43 g (2.16 mmol) of p-nitrophenyl chloroformate in solution in 5 ml of dichloroethane. The mixture is then stirred at room temperature for 2 hours then a solution of 0.5 g (1.97 mmol) of tert-butyl (3aR,5r,6aS)-5-(2-aminoethyl)hexahydrocyclopenta[c]pyrrole-2(1H)-carboxylate, obtained in step 6.1., and 0.34 ml (1.97 mmol) of N,N-diisopropylethylamine are added. The mixture is then heated at 70° C. for 3 hours.

After returning to room temperature, water is added then the aqueous phase is extracted several times with dichloromethane. The combined organic phases are then successively washed with a 1M aqueous solution of sodium hydroxide (three times) then with a saturated aqueous solution of ammonium chloride (twice). The organic phase is dried over sodium sulphate, filtered and evaporated to dryness. After purification on a silica gel column eluting with a 99/1 then 97/3 mixture of dichloromethane and methanol, 0.44 g of pure product is obtained in the form of an orange oil.

LC-MS: M+H=452

$^1$H NMR (DMSO) δ(ppm): 7.40 (broad s, 1H), 6.36 (s, 1H), 5.19 (s, 2H), 4.37 (q, 2H), 3.32 (m, 2H), 3.08 (m, 2H), 2.98 (m, 2H), 2.52 (m, 2H), 2.00 (m, 2H), 1.83 (m, 1H), 1.46 (m, 2H), 1.38 (s, 9H), 1.32 (t, 3H), 0.90 (m, 2H).

6.3. Ethyl 5-{[({2-[(3aR,5r,6aS)-2-(5-bromopyrid-2-yl)octa-hydrocyclopenta[c]pyrrol-5-yl]ethyl}carbamoyl)oxy]methyl}-isoxazole-3-carboxylate The procedure described in Example 1, step 1.4 is followed. Starting from 0.44 g (0.97 mmol) of tert-butyl (3aR,5r,6aS)-5-{2-[({[3-(ethoxycarbonyl)isoxazol-5-yl]methoxy}carbonyl)-amino]ethyl}hexahydrocyclopenta[c]pyrrole-2(1H)-carboxylate, obtained in step 6.2. and 0.82 ml (9.74 mmol) of trifluoro-acetic acid, ethyl 5-{[({2-[(3aR,5r,6aS)-octahydrocyclo-penta[c]pyrrol-5-yl]ethyl}carbamoyl)oxy]methyl}isoxazole-3-carboxylate is obtained in trifluoroacetate form, used as is in the following step according to the procedure described in Example 1, step 1.5.

Starting from 0.45 g (0.97 mmol) of ethyl 5-{[({2-[(3aR,5r,6aS)-octahydrocyclopenta[c]pyrrol-5-yl]ethyl}-carbamoyl)oxy]methyl}isoxazole-3-carboxylate, obtained previously, 0.51 ml (2.91 mmol) of N,N-diisopropylethylamine, and 0.17 g (0.97 mmol) of 5-bromo-2-fluoropyridine, and after chromatography on silica gel eluting with a 99/1 to 98/2 mixture of dichloromethane and methanol, 0.19 g of pure product is obtained in the form of a white solid.

Melting point (° C.): 105-107° C.

LC-MS: M+H=507

$^1$H NMR (DMSO) δ(ppm): 8.10 (d, 1H), 7.61 (d, 1H), 7.45 (broad t, 1H), 6.86 (s, 1H), 6.45 (d, 1H), 5.19 (s, 2H), 4.37 (q, 2H), 3.42 (m, 2H), 3.28 (m, 2H), 3.00 (m, 2H), 2.68 (m, 2H), 2.11 (m, 2H), 1.89 (m, 1H), 1.54 (m, 2H), 1.31 (t, 3H), 0.97 (m, 2H).

6.4. [3-(methylcarbamoyl)isoxazol-5-yl]methyl {2-[(3aR,5r,6aS)-2-(5-bromopyrid-2-yl)octahydrocyclopenta[c]-pyrrol-5-yl]ethyl}carbamate 0.070 g (0.14 mmol) of ethyl 5-{[({2-[(3aR,5r,6aS)-2-(5-bromopyrid-2-yl)octahydrocyclopenta[c]pyrrol-5-yl]ethyl}-carbamoyl)oxy]methyl}isoxazole-3-carboxylate, obtained in step 6.3., is put into solution in 1.7 ml of a 8M solution of methylamine in ethanol. The mixture is stirred at room temperature for 2 hours then evaporated to dryness. After high-temperature recrystallization in ether, 0.031 g of product is obtained in the form of a white solid.

Melting point (° C.): 157-159° C.

LC-MS: M+H=492

$^1$H NMR (DMSO) δ(ppm): 8.67 (m, 1H), 8.10 (d, 1H), 7.60 (dd, 1H), 7.39 (broad t, 1H), 6.74 (s, 1H), 6.45 (d, 1H), 5.16 (s, 2H), 3.40 (m, 2H), 3.22 (m, 2H), 3.00 (m, 2H), 2.97 (d, 3H), 2.75 (m, 2H), 2.10 (m, 2H), 1.89 (m, 1H), 1.46 (m, 2H), 0.98 (m, 2H).

EXAMPLE 7

Compound No. 12

(3-Carbamoylisoxazol-5-yl)methyl {[(3aR,5r,6aS)-5-fluoro-2-(6-fluoroquinolin-2-yl)octahydrocyclopenta[c]pyrrol-5-yl]-methyl}carbamate (exo)

7.1. tert-Butyl (3aR,5r,6aS)-5-cyano-5-hydroxyhexahydro-cyclopenta[c]pyrrole-2(1H)-carboxylate 1.0 g (4.44 mmol) of tert-butyl (3aR,6aS)-5-oxohexahydro-cyclopenta[c]pyrrole-2(1H)-carboxylate (*Tetrahedron*, 1993, 49(23), 5047-54) are put into solution in 5 ml of a water/methanol (1/1) mixture. The reaction medium is cooled to 0° C. then 0.21 g (4.44 mmol) of sodium cyanide and 0.47 g (8.44 mmol) of ammonium chloride are added. The mixture is stirred at room temperature for 20 hours.

It is evaporated to dryness then the residue is taken up with dichloromethane and water. The aqueous phase is extracted several times with dichloromethane. The combined organic phases are dried over sodium sulphate, filtered and evaporated to dryness. Thus, 0.59 g of product is obtained in the form of a white solid, used as is in the following step.

Melting point (° C.): 168-170° C.

$^1$H NMR (DMSO) δ (ppm): 6.34 (broad s, 1H), 3.40 (m, 2H), 3.20 (m, 2H), 2.82 (m, 2H), 2.28 (m, 2H), 1.82 (m, 2H), 1.40 (s, 9H).

7.2. tert-Butyl (3aR,5r,6aS)-5-cyano-5-fluorohexahydrocyclo-penta[c]pyrrole-2(1H)-carboxylate A solution of 0.50 g (1.98 mmol) of tert-butyl (3aR,5r,6aS)-5-cyano-5-hydroxyhexahydrocyclopenta[c]pyrrole-2(H)-carboxylate, obtained in step 7.1., 0.32 g (1.98 mmol) of diethylaminosulphur trifluoride (DAST) in 6 ml of dichloromethane is stirred at room temperature for 30 minutes.

A saturated aqueous solution of sodium hydrogen carbonate is added, then the aqueous phase is extracted several times with dichloromethane. The combined organic phases are dried over sodium sulphate, filtered and evaporated to dryness. Thus, 0.47 g of product is obtained in the form of an orange oil, used as is in the following step.

MS: M+H=255

$^{19}$F NMR (DMSO) δ (ppm): −142.58

7.3. tert-Butyl (3aR,5r,6aS)-5-(aminomethyl)-5-fluorohexa-hydrocyclopenta[c]pyrrole-2(1H)-carboxylate Added slowly to a solution of 0.47 g (1.85 mmol) of tert-butyl (3aR,5r,6aS)-5-cyano-5-fluorohexahydrocyclopenta[c]-pyrrole-2(1H)-carboxylate, obtained in step 7.2., in 4 ml of tetrahydrofuran, cooled to 0° C., are 7.39 ml (7.39 mmol) of a 1M solution of borane in tetrahydrofuran. The mixture is stirred at 0° C. for 1 hour then ethanol is slowly added. The stirring is continued for around 3 minutes.

It is allowed to return to room temperature then evaporated to dryness. The residue obtained is taken up with a saturated aqueous solution of ammonium chloride and dichloromethane. The aqueous phase is extracted several times with dichloromethane. The combined organic phases are dried over sodium sulphate, filtered and evaporated to dryness.

Thus, 0.42 g of product is obtained, used as is in the following step.

LC-MS: M+H=259
$^{19}$F NMR (DMSO) δ (ppm): −143.43

7.4. tert-Butyl (3aR,5r,6aS)-5-{[({[3-(ethoxycarbonyl)-isoxazol-5-yl]methoxy}carbonyl)amino]methyl}-5-fluoro-hexahydrocyclopenta[c]pyrrole-2(1H)-carboxylate The procedure described in Example 3, step 3.4. is followed. Starting from 0.40 g (1.55 mmol) of tert-butyl (3aR,5r,6aS)-5-(aminomethyl)-5-fluorohexahydrocyclopenta[c]pyrrole-2(1H)-carboxylate, obtained in step 7.3., 0.26 g (1.55 mmol) of ethyl 5-hydroxymethylisoxazole-3-carboxylate, 0.54 ml (3.10 mmol) of N,N-diisopropylethylamine and 0.31 g (1.55 mmol) of para-nitrophenyl chloroformate, 0.18 g of product is obtained in the form of a colourless oil.

LC-MS: M+H=455
$^1$H NMR (DMSO) δ (ppm): 7.76 (broad t, 1H), 6.90 (s, 1H), 5.25 (s, 2H), 4.38 (q, 2H), 3.38 (m, 2H), 3.30 (m, 2H), 3.18 (m, 2H), 2.70 (m, 2H), 2.05 (m, 2H), 1.74 (m, 2H), 1.40 (s, 9H), 1.33 (t, 3H).

7.5. Ethyl 5-{[({[(3aR,5r,6aS)-5-fluoro-2-(6-fluoro-quinolin-2-yl)octahydrocyclopenta[c]pyrrol-5-yl]methyl}carbamoyl)-oxy]methyl}isoxazole-3-carboxylate The procedure described in Example 1, step 1.4. is followed. Starting from 0.17 g (0.37 mmol) of tert-butyl (3aR,5r,6aS)-5-{[({[3-(ethoxycarbonyl)isoxazol-5-yl]methoxy}carbonyl)-amino]methyl}-5-fluorohexahydrocyclopenta[c]pyrrole-2(1H)-carboxylate, obtained in step 7.4., and 0.31 ml (0.425 mmol) of trifluoroacetic acid, the amine ethyl 5-{[({[(3aR,5r,6aS)-5-fluorooctahydrocyclopenta[c]pyrrol-5-yl]methyl}carbamoyl)oxy]methyl}isoxazole-3-carboxylate is obtained in trifluoroacetate form, used as is in the following step according to the procedure described in Example 1, step 1.5.

Starting from 0.17 g (0.37 mmol) of ethyl 5-{[({[(3aR,5r,6aS)-5-fluorooctahydrocyclopenta[c]pyrrol-5-yl]methyl}carbamoyl)oxy]methyl}isoxazole-3-carboxylate, obtained previously, 0.19 ml (1.11 mmol) of N,N-diisopropyl-ethylamine and 0.08 g (0.37 mmol) of 2-bromo-6-fluoroquinoline, and by eluting with a 99/1 to 97/3 mixture of dichloromethane and methanol, 0.08 g of product is obtained in the form of a white solid.

Melting point (° C.): 130-132° C.
LC-MS: M+H=501
$^1$H NMR (DMSO) δ (ppm): 8.00 (d, 1H), 7.80 (broad t, 1H), 7.59 (m, 1H), 7.50 (dd, 1H), 7.39 (m, 1H), 7.00 (d, 1H), 6.90 (s, 1H), 5.25 (s, 2H), 4.38 (q, 2H), 3.80 (m, 2H), 3.50 (m, 2H), 3.37 (m, 2H), 2.90 (m, 2H), 2.15 (m, 2H), 1.85 (m, 2H), 1.30 (t, 3H).

7.6. (3-Carbamoylisoxazol-5-yl)methyl {[(3aR,5r,6aS)-5-fluoro-2-(6-fluoroquinolin-2-yl)octahydrocyclopenta[c]-pyrrol-5-yl]methyl}carbamate The procedure described in Example 6, step 6.4. is followed. Starting from 0.07 g (0.15 mmol) of ethyl 5-{[({[(3aR,5r,6aS)-5-fluoro-2-(6-fluoroquinolin-2-yl)octa-hydrocyclopenta[c]-pyrrol-5-yl]methyl}carbamoyl)oxy]methyl}-isoxazole-3-carboxylate, obtained in step 7.5., and 2.14 ml of a 7M solution of ammonia in methanol, and after high-temperature crystallization in diethyl ether, 0.04 g of product is obtained in the form of a white solid.

Melting point (° C.): 228-230
LC-MS: M+H=472
$^1$H NMR (DMSO) δ (ppm): 8.13 (broad s, 1H), 8.00 (d, 1H), 7.83 (broad s, 1H), 7.77 (broad t, 1H), 7.58 (m, 1H), 7.50 (m, 1H), 7.39 (m, 1H), 6.96 (d, 1H), 6.77 (s, 1H), 5.23 (s, 2H), 3.80 (m, 2H), 3.50 (m, 2H), 3.38 (m, 2H), 2.90 (m, 2H), 2.15 (m, 2H), 1.85 (m, 2H).

EXAMPLE 8

Compound No. 14

[3-(Methylcarbamoyl)isoxazol-5-yl]methyl [3-(6-fluoro-quinolin-2-yl)-3-azabicyclo[3.1.0]hex-6-yl] carbamate

8.1 tert-Butyl 6-[({[3-(ethoxycarbonyl)isoxazol-5-yl]-methoxy}carbonyl)amino]-3-azabicyclo[3.1.0]hexane-3-carboxylate The procedure described in Example 3, step 3.4. is followed. Starting from 3.00 g (15.13 mmol) of tert-butyl 6-amino-3-azabicyclo[3.1.0]hexane-3-carboxylate, 2.58 g (15.13 mmol) of ethyl 5-hydroxymethyl-isoxazole-3-carboxylate, 5.27 ml (30.26 mmol) of N,N-diisopropylethylamine and 3.05 g (15.13 mmol) of para-nitrophenyl chloroformate, 4.50 g of product are obtained in the form of a colourless oil (75%).

LC-MS: M−H=394
$^1$H NMR (DMSO) δ (ppm): 7.72 (s broad, 1H), 6.90 (s, 1H), 5.22 (s, 2H), 4.40 (q, 2H), 3.45 (m, 2H), 3.32 (m, 2H), 2.19 (m, 1H), 1.68 (m, 2H), 1.40 (s, 9H), 1.32 (t, 3H)

8.2 Ethyl 5-[({[3-(6-fluoroquinolin-2-yl)-3-azabicyclo-[3.1.0]hex-6-yl]carbamoyl}oxy)methyl]isoxazole-3-carboxylate The procedure described in Example 1, step 1.4. is followed. Starting from 4.50 g (11.38 mmol) of tert-butyl 6-[({[3-(ethoxycarbonyl)isoxazol-5-yl]methoxy}carbonyl)amino]-3-aza-bicyclo[3.1.0]hexane-3-carboxylate and 9.59 ml (113.81 mol) of trifluoroacetic acid, the amine ethyl 5-{[(3-azabicycle-[3.1.0]hex-6-ylcarbamoyl)oxy]methyl}isoxazole-3-carboxylate is obtained in trifluoroacetate form, used as is in the following step according to the procedure described in Example 1, step 1.5.

Starting from 1.55 g (3.79 mmol) of ethyl 5-{[(3-azabicyclo[3.1.0]hex-6-ylcarbamoyl)oxy]methyl}isoxazole-3-carboxylate in trifluoroacetate form, 1.98 ml (11.37 mmol) of N,N-diisopropylethylamine, and 0.68 g (3.79 mmol) of 2-chloro-6-fluoro-quinoline, and eluting with a 99/1 to 98/2 mixture of dichloromethane and methanol, 0.61 g (36%) of product is obtained in the form of an orange oil.

LC-MS: M+H=441
$^1$H NMR (DMSO) δ (ppm): 8.01 (d, 1H), 7.80 (s broad, 1H), 7.64 (m, 1H), 7.50 (m, 1H), 7.40 (m, 1H), 6.95 (m, 2H), 5.25 (s, 2H), 4.38 (q, 2H), 3.85 (m, 2H), 3.55 (m, 2H), 2.35 (m, 1H), 1.90 (m, 2H), 1.30 (m, 3H)

8.3 [3-(Methylcarbamoyl)isoxazol-5-yl]methyl [3-(6-fluoro-quinolin-2-yl)-3-azabicyclo[3.1.0]hex-6-yl]carbamate The procedure described in Example 6, step 6.4. is followed. Starting from 0.30 g (0.68 mmol) of ethyl 5-[({[3-(6-fluoro-quinolin-2-yl)-3-azabicyclo[3.1.0]hex-6-yl]carbamoyl}oxy)-methyl]isoxazole-3-carboxylate and 8.50 ml of an 8M solution of methylamine in ethanol, and after high-temperature crystallization in diethyl ether, 0.17 g (60%) of product is obtained in the form of a white solid.

Melting point (° C.): 220-222° C.

LC-MS: M+H=426

$^1$H NMR (DMSO) δ (ppm): 8.73 (broad s, 1H), 8.04 (d, 1H), 7.80 (broad s, 1H), 7.62 (m, 1H), 7.54 (m, 1H), 7.42 (m, 1H), 6.97 (d, 1H), 6.81 (s, 1H), 5.22 (m, 2H), 3.86 (m, 2H), 3.57 (m, 2H), 2.80 (d, 3H), 2.35 (m, 1H), 1.90 (m, 2H)

Table 1 that follows illustrates the chemical structures and physical properties of a few compounds according to the invention.

In this table all the compounds are in free base form.

TABLE 1

(I)

| No. | R$_1$ | m | n | o | p | A | R$_2$ | R$_3$ | R$_4$ | endo or exo |
|---|---|---|---|---|---|---|---|---|---|---|
| 1. | 6-(trifluoromethyl)pyridin-3-yl | 1 | 1 | 1 | 1 | CH$_2$ | H | H | 4-methylthiazol-2-yl | exo |
| 2. | 5-bromo-6-methylpyridin-3-yl | 1 | 1 | 1 | 1 | CH$_2$ | H | H | 4-methylthiazol-2-yl | exo |
| 3. | 6-(4-fluorophenyl)pyridin-3-yl | 1 | 1 | 1 | 1 | CH$_2$ | H | H | 4-methylthiazol-2-yl | exo |
| 4. | 6-(1-methyl-1H-pyrazol-4-yl)pyridin-3-yl | 1 | 1 | 1 | 1 | CH$_2$ | H | H | 4-methylthiazol-2-yl | exo |
| 5. | 6-(trifluoromethyl)pyridin-2-yl | 1 | 1 | 1 | 1 | bond | H | H | 4-methylthiazol-2-yl | exo |
| 6. | 6-fluoroquinolin-2-yl | 1 | 1 | 1 | 1 | bond | H | H | 4-methylthiazol-2-yl | exo |

TABLE 1-continued (I)

| No. | R₁ | m | n | o | p | A | R₂ | R₃ | R₄ | endo or exo |
|---|---|---|---|---|---|---|---|---|---|---|
| 7. | 4-F-phenyl-pyridinyl (F-C₆H₄ at 5-position of 2-methylpyridine) | 1 | 1 | 1 | 1 | CH₂ | H | H | 5-methyl-1-methyl-1,2,4-triazol-3-yl | exo |
| 8. | 5-F-pyridin-3-yl linked to 6-methylpyridin-2-yl | 1 | 1 | 1 | 1 | CH₂ | H | H | 5-methyl-1-methyl-1,2,4-triazol-3-yl | exo |
| 9. | 4-F-phenyl-(6-methylpyridin-3-yl) | 1 | 1 | 1 | 1 | CH₂ | H | H | 5-methylisoxazol-3-yl-CONH₂ | exo |
| 10. | 5-Br-2-methylpyridin-3-yl | 1 | 1 | 1 | 1 | (CH₂)₂ | H | H | 5-methylisoxazol-3-yl-CONHMe | endo |
| 11. | 5-Br-2-methylpyridin-3-yl | 1 | 1 | 1 | 1 | (CH₂)₂ | H | H | 5-methylisoxazol-3-yl-CONH₂ | endo |
| 12. | 6-F-2-methylquinolinyl | 1 | 1 | 1 | 1 | CH₂ | F | H | 5-methylisoxazol-3-yl-CONH₂ | exo |
| 13. | 6-F-2-methylquinolinyl | 1 | 1 | 1 | 1 | CH₂ | H | H | 5-methylisoxazol-3-yl-CONHMe | exo |
| 14. | 6-F-2-methylquinolinyl | 1 | 0 | 0 | 1 | bond | H | H | 5-methylisoxazol-3-yl-CONHMe | — |

TABLE 1-continued

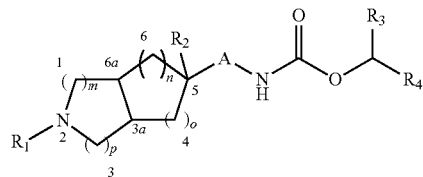

| No. | R₁ | m | n | o | p | A | R₂ | R₃ | R₄ | endo or exo |
|---|---|---|---|---|---|---|---|---|---|---|
| 15. | 4-F-phenyl-pyridinyl-methyl | 1 | 0 | 0 | 1 | bond | H | H | 5-methyl-isoxazol-3-yl-CO₂Et | — |
| 16. | 6-F-2-methylquinolinyl | 1 | 0 | 0 | 1 | bond | H | H | 5-methyl-isoxazol-3-yl-CONH₂ | — |
| 17. | 4-F-phenyl-pyridinyl-methyl | 1 | 0 | 0 | 1 | bond | H | H | 5-methyl-isoxazol-3-yl-CONH₂ | — |
| 18. | 4-F-phenyl-pyridinyl-methyl | 1 | 0 | 0 | 1 | bond | H | H | 5-methyl-isoxazol-3-yl-CONHMe | — |
| 19. | 4-F-phenyl-pyridinyl-methyl | 1 | 0 | 0 | 1 | bond | H | H | 5-methyl-isoxazol-3-yl-CONMe₂ | — |

Table 2 that follows gives the results of the ¹H NMR analyses, the melting points (MP) and the M+H masses measured for the compounds of Table 1.

TABLE 2

| No. | ¹H NMR (DMSO, 400 MHZ) | MP | M + H |
|---|---|---|---|
| 1. | 9.10 (s, 1H), 7.69 (m, 2H), 7.32 (broad t, 1H), 7.00 (d, 1H), 6.76 (d, 1H), 5.12 (s, 2H), 3.60 (m, 2H), 3.21 (m, 2H), 3.00 (m, 2H), 2.82 (m, 2H), 2.22 (m, 1H), 1.60 (4H) | 97-99° C. | 427 |
| 2. | 9.10 (s, 1H), 8.12 (s, 1H), 7.65 (m, 2H), 7.30 (broad s, 1H), 6.48 (d, 1H), 5.12 (s, 2H), 3.53 (m, 2H), 3.15 (m, 2H), 2.96 (m, 2H), 2.82 (m, 2H), 2.21 (m, 1H), 1.58 (m, 4H) | 114-116° C. | 437 |
| 3. | 9.10 (s, 1H), 8.38 (s, 1H), 7.80 (d, 1H), 7.61 (m, 3H), 7.32 (broad s, 1H), 7.21 (m, 2H), 6.58 (d, 1H), 5.11 (s, 2H), 3.60 (m, 2H), 3.12 (m, 2H), 2.99 (m, 2H), 2.81 (m, 2H), 2.21 (m, 1H), 1.56 (m, 4H) | 129-131° C. | 453 |
| 4. | 9.10 (s, 1H), 8.30 (s, 1H), 8.00 (s, 1H), 7.75 (s, 1H), 7.65 (m, 2H), 7.31 (broad t, 1H), 6.48 (d, 1H), 5.12 (s, 2H), 3.85 (s, 3H), 3.55 (m, 2H), 3.18 (m, 2H), 3.00 (m, 2H), 2.80 (m, 2H), 2.20 (m, 1H), 1.60 (4H) | 120-122° C. | 439 |
| 5. | 9.11 (s, 1H), 7.70 (m, 2H), 7.40 (m, 1H), 7.01 (d, 1H), 6.78 (d, 1H), 5.12 (s, 2H), 4.00 (m, 1H), 3.58 (m, 2H), 3.28 (m, 2H), 2.90 (m, 2H), 1.78 (m, 4H) | 148-150° C. | 413 |
| 6. | 9.11 (s, 1H), 8.02 (d, 1H), 7.68 (broad s, 1H), 7.60 (m, 1H), 7.51 (m, 1H), 7.41 (m, 2H), 7.00 (d, 1H), 5.10 (s, 2H), 4.05 (m, 1H), 3.70 (m, 2H), 3.40 (m, 2H), 2.90 (m, 2H), 1.80 (m, 4H) | 176-178° C. | 413 |
| 7. | 8.40 (s, 1H), 7.91 (s, 1H), 7.80 (d, 1H), 7.62 (m, 2H), 7.45 (broad s, 1H), 7.25 (m, 2H), 6.57 (d, 1H), 5.15 (s, 2H), 3.88 (s, 3H), 3.60 (m, 2H), 3.20 (m, 2H), 2.99 (m, 2H), 2.81 (m, 2H), 2.21 (m, 1H), 1.60 (m, 4H) | 124-126° C. | 451 |
| 8. | 9.15 (s, 1H), 8.60 (s, 1H), 8.30 (m, 1H), 7.90 (s, 1H), 7.62 (m, 1H), 7.45 (broad s, 1H), 7.31 (m, 1H), 6.57 (d, 1H), 5.15 (s, 2H), 3.88 (s, 3H), 3.68 (m, 2H), 3.28 (m, 2H), 2.99 (m, 2H), 2.85 (m, 2H), 2.25 (m, | 136-138° C. | 452 |

TABLE 2-continued

| No. | ¹H NMR (DMSO, 400 MHZ) | MP | M + H |
|---|---|---|---|
|  | 1H), 1.60 (m, 4H) | | |
| 9 | 8.40 (s, 1H), 7.95 (broad s, 1H), 7.78 (d, 1H), 7.68 (broad s, 1H), 7.60 (m, 2H), 7.35 (broad s, 1H), 7.22 (m, 2H), 6.75 (s, 1H), 6.52 (d, 1H), 5.19 (s, 2H), 3.61 (m, 2H), 3.22 (m, 2H), 3.01 (m, 2H), 2.82 (m, 2H), 2.25 (m, 1H), 1.60 (m, 4H) | 208-210° C. | 480 |
| 10 | 8.67 (m, 1H), 8.10 (d, 1H), 7.60 (dd, 1H), 7.39 (broad t, 1H), 6.74 (s, 1H), 6.45 (d, 1H), 5.16 (s, 2H), 3.40 (m, 2H), 3.22 (m, 2H), 3.00 (m, 2H), 2.97 (d, 3H), 2.75 (m, 2H), 2.10 (m, 2H), 1.89 (m, 1H), 1.46 (m, 2H), 0.98 (m, 2H) | 157-159° C. | 492 |
| 11 | 8.10 (m, 2H), 7.80 (broad s, 1H), 7.60 (m, 1H), 7.39 (broad t, 1H), 6.73 (s, 1H), 6.45 (d, 1H), 5.16 (s, 2H), 3.41 (m, 2H), 3.26 (m, 2H), 3.00 (m, 2H), 2.68 (m, 2H), 2.09 (m, 2H), 1.89 (m, 1H), 1.47 (m, 2H), 1.00 (m, 2H) | 182-184° C. | 478 |
| 12 | 8.13 (broad s, 1H), 8.00 (d, 1H), 7.83 (broad s, 1H), 7.77 (broad t, 1H), 7.58 (m, 1H), 7.50 (m, 1H), 7.39 (m, 1H), 6.96 (d, 1H), 6.77 (s, 1H), 5.23 (s, 2H), 3.80 (m, 2H), 3.50 (m, 2H), 3.38 (m, 2H), 2.90 (m, 2H), 2.15 (m, 2H), 1.85 (m, 2H) | 228-230° C. | 472 |
| 13 | 8.69 (broad s, 1H), 8.00 (d, 1H), 7.57 (m, 1H), 7.50 (m, 2H), 7.40 (m, 1H), 6.96 (d, 1H), 6.76 (s, 1H), 5.19 (s, 2H), 3.73 (m, 2H), 3.31 (m, 2H), 2.99 (m, 2H), 2.84 (m, 2H), 2.78 (s, 3H), 2.24 (m, 1H), 1.65 (m, 2H), 1.56 (m, 2H) | 169-171° C. | 468 |
| 14 | 8.73 (broad s, 1H), 8.04 (d, 1H), 7.80 (broad s, 1H), 7.62 (m, 1H), 7.54 (m, 1H), 7.42 (m, 1H), 6.97 (d, 1H), 6.81 (s, 1H), 5.22 (m, 2H), 3.86 (m, 2H), 3.57 (m, 2H), 2.80 (d, 3H), 2.35 (m, 1H), 1.90 (m, 2H) | 220-222° C. | 426 |
| 15 | 8.40 (s, 1H), 7.82 (m, 2H), 7.64 (m, 2H), 7.25 (m, 2H), 6.94 (s, 1H), 6.55 (d, 1H), 5.24 (s, 2H), 4.40 (q, 2H), 3.74 (m, 2H), 3.45 (m, 2H), 2.34 (m, 1H), 1.88 (m, 2H), 1.35 (t, 3H) | 183-185° C. | 467 |
| 16 | 8.12 (broad s, 1H), 8.00 (d, 1H), 7.84 (broad s, 2H), 7.60 (m, 1H), 7.50 (m, 1H), 7.41 (m, 1H), 6.95 (d, 1H), 6.80 (s, 1H), 5.20 (m, 2H), 3.85 (m, 2H), 3.57 (m, 2H), 2.35 (m, 1H), 1.88 (m, 2H) | 206-208° C. | 412 |
| 17 | 8.40 (s, 1H), 8.15 (broad s, 1H), 7.83 (m, 3H), 7.68 (m, 2H), 7.30 (m, 2H), 6.80 (s, 1H), 6.55 (d, 1H), 5.20 (s, 2H), 3.72 (m, 2H), 3.44 (m, 2H), 2.33 (m, 1H), 1.88 (m, 2H) | 228-230° C. | 438 |
| 18 | 8.70 (broad s, 1H), 8.40 (s, 1H), 7.80 (m, 2H), 7.61 (m, 2H), 7.25 (m, 2H), 6.80 (s, 1H), 6.55 (d, 1H), 5.20 (s, 2H), 3.73 (m, 2H), 3.42 (m, 2H), 2.78 (s, 3H), 2.33 (m, 1H), 1.87 (m, 2H) | 217-219° C. | 452 |
| 19 | 8.38 (s, 1H), 7.81 (m, 2H), 7.62 (m, 2H), 7.28 (m, 2H), 6.74 (s, 1H), 6.55 (d, 1H), 5.22 (s, 2H), 3.72 (m, 2H), 3.42 (m, 2H), 3.10 (s, 3H), 3.01 (s, 3H), 2.31 (m, 1H), 1.88 (m, 2H) | 195-197° C. | 466 |

The compounds of the invention underwent pharmacological tests to determine their inhibitory effect on the enzyme FAAH (Fatty Acid Amide Hydrolase).

Protocol 1

The inhibitory activity was demonstrated in a radioenzymatic test based on measuring the product of hydrolysis of anandamide [ethanolamine 1-³H] with FAAH (*Life Sciences* (1995), 56, 1999-2005 and *Journal of Biochemical and Biophysical Methods* (2004), 60(2), 171-177). Thus, mouse brains (minus the cerebellum) are removed and stored at −80° C. The membrane homogenates are prepared extemporaneously by homogenizing the tissues using a Precellys® machine in reaction buffer (10 mM Tris-HCl, pH=8, 150 mM NaCl and 1 mM ethylenediaminetetraacetic acid (EDTA)). The enzymatic reaction is performed in 96-well Multiscreen filtration plates in a final volume of 70 μl. Reaction buffer supplemented with fatty acid-free bovine serum albumin (BSA, 1 mg/ml) is used for the enzymatic reaction and the dilution of the compounds and of the anandamide [ethanolamine 1-³H]. The reaction buffer containing BSA (43 μl/well), the diluted test compounds at various concentrations (7 μl/well containing 1% DMSO) and the membrane preparation (10 μl/well, i.e. 200 μg of tissue per test) are successively added to the wells. After preincubation for 20 minutes of the compounds with the enzyme at 25° C., the reaction is started by adding anandamide [ethanolamine 1-³H](specific activity of 15-20 Ci/mmol) diluted with cold anandamide (10 μl/well, final concentration of 10 μM, 0.01 μCi per test). After incubation for 20 minutes at 25° C., the enzymatic reaction is stopped by adding a 5M solution of activated carbon prepared in 1.5M NaCl buffer and 0.5M HCl (50 μl/well). The mixture is stirred for 10 minutes then the aqueous phase containing the ethanolamine [1-³H] is recovered by filtration under vacuum and counted by liquid scintillation.

Protocol 2

The inhibitory activity was demonstrated via a fluorescent technique in an enzymatic test based on measuring the fluorescent product of hydrolysis of arachidonoyl 7-amino-4-methylcoumarin amide (AAMC) with FAAH (Analytical Biochemistry (2005), 343:143-151, J. of Biomolecular Screening (2006), 11(5):519-527 and J. of Neurosciences Methods (2007), 161:47-54). Thus, mouse brains (minus the cerebellum) are withdrawn and stored at −80° C. The brain homogenates are prepared extemporaneously by homogenizing the tissues using a Precellys® machine in reaction buffer (10 mM Tris-HCl, pH=8, 150 mM NaCl and 1 mM ethylenediamine-tetraacetic acid (EDTA)). The enzymatic reaction is performed in black polystyrene 384-well plates in a final volume of 50 μL. Reaction buffer supplemented with fatty acid-free bovine serum albumin (BSA, 1 mg/ml) is used for the enzymatic reaction, the dilution of the compounds and the dilution of the AAMC. Reaction buffer containing the BSA (25 μl/well), the diluted test compounds at various concentrations (5 μl/well containing 1% DMSO) and the membrane preparation (10 μL/well, i.e. 200 μg of tissue per test) are successively added to the wells. After preincubation for 20 minutes of the compounds with the enzyme at 25° C., the reaction is started by adding 10 μL of substrate per well (AAMC, final concentration of 10 μM). After incubation for 40 minutes at 37° C., the aminomethyl coumarin (AMC) produced is measured by fluorescent counting (Envision plate reader).

Under the conditions of protocol 1, the most active compounds of the invention have $IC_{50}$ values (concentration that inhibits 50% of the control enzymatic activity of FAAH) of between 0.001 μM and 1 μM. For example, compounds Nos. 1, 3, 4, 7, 8, 10 and 12 have respective $IC_{50}$ values of 200 nM, 0.98 nM, 8.5 nM, 170 nM, 1.1 nM and 2.4 nM.

Under the conditions of protocol 2, the most active compounds of the invention have $IC_{50}$ values (concentration that inhibits 50% of the control enzymatic activity of FAAH) of between 0.001 μM and 1 μM. For example, compound No. 14 has a respective $IC_{50}$ value of 12 nM.

It thus appears that the compounds according to the invention have an inhibitory activity on the enzyme FAAH.

The in vivo activity of the compounds of the invention can be evaluated in a test of analgesia.

Thus, the intraperitoneal (i.p.) administration of PBQ (phenylbenzoquinone, 2 mg/kg in a 0.9% sodium chloride solution containing 5% ethanol) to male OF1 mice weighing 25 to 30 g causes abdominal stretching, on average 30 torsions or contractions within a period of 5 to 15 minutes after injection. The test compounds are administered orally (p.o.) or intraperitoneally (i.p.) suspended in Tween 80 at 0.5%, 60 minutes or 120 minutes before the administration of PBQ. Under these conditions, the most powerful compounds reduce by 35% to 80% the number of stretches induced with PBQ, over a dose range of between 1 and 30 mg/kg.

The enzyme FAAH (*Chemistry and Physics of Lipids*, (2000), 108, 107-121) catalyses the hydrolysis of the endogenous derivatives of amides and esters of various fatty acids such as N-arachidonoylethanolamine (anandamide), N-palmitoyl-ethanolamine, N-oleoylethanolamine, oleamide or 2-arachidonoylglycerol. These derivatives exert different pharmacological activities by interacting, inter alia, with the cannabinoid and vanilloid receptors.

The compounds of the invention block this degradation pathway and increase the tissue content of these endogenous substances. In this respect, they may be used in the prevention and treatment of pathologies in which the endogenous cannabinoids and/or any other substrate metabolized by the enzyme FAAH are involved. Mention may be made, for example, of the following diseases and complaints: pain, especially acute or chronic pain of neurogenic type: migraine, neuropathic pain including the forms associated with the herpes virus and diabetes and chemotherapy, acute or chronic pain associated with inflammatory diseases: arthritis, rheumatoid arthritis, osteoarthritis, spondylitis, gout, vascularitis, Crohn's disease, irritable bowel syndrome, acute or chronic peripheral pain, vertigo, vomiting, nausea, in particular post-chemotherapy nausea, eating disorders, in particular anorexia and cachexia of diverse nature, neurological and psychiatric pathologies: tremor, dyskinaesia, dystonia, spasticity, compulsive and obsessive behaviour, Tourette's syndrome, all forms of depression and anxiety of any nature or origin, mood disorders, psychoses, acute and chronic neurodegenerative diseases: Parkinson's disease, Alzheimer's disease, senile dementia, Huntington's chorea, lesions associated with cerebral ischaemia and cranial and medullary trauma, epilepsy, sleep disorders, including sleep apnoea, cardiovascular diseases, in particular hypertension, cardiac arrhythmia, arteriosclerosis, heart attack, cardiac ischaemia, renal ischaemia, cancers: benign skin tumours, papillomas and cerebral tumours, prostate tumours, cerebral tumours (gliobastomas, medullo-epitheliomas, medullo-blastomas, neuroblastomas, tumours of embryonic origin, astrocytomas, astroblastomas, ependyomas, oligodendro-gliomas, plexus tumour, neuroepitheliomas, pineal gland tumours, ependymoblastomas, malignant meningiomas, sarcomatoses, malignant melanomas, schwennomas), immune system disorders, especially autoimmune diseases: psoriasis, lupus erythematosus, connective tissue diseases, Sjögrer's syndrome, ankylosing spondylitis, undifferentiated spondylitis, Behcet's disease, haemolytic autoimmune anaemias, multiple sclerosis, amyotrophic lateral sclerosis, amylosis, graft rejection, diseases affecting the plasmocytic line, allergic diseases: immediate or delayed hypersensitivity, allergic rhinitis or allergic conjunctivitis, contact dermatitis, parasitic, viral or bacterial infectious diseases: AIDS, meningitis, inflammatory diseases, especially articular diseases: arthritis, rheumatoid arthritis, osteoarthritis, spondylitis, gout, vascularitis, Crohn's disease, irritable bowel syndrome, osteoporosis, ocular complaints: ocular hypertension, glaucoma, pulmonary complaints: respiratory pathway diseases, bronchospasms, coughing, asthma, chronic bronchitis, chronic obstruction of the respiratory pathways, emphysema, gastrointestinal diseases: irritable bowel syndrome, intestinal inflammatory disorders, ulcers, diarrhoea, urinary incontinence and inflammation of the bladder.

The use of the compounds according to the invention, in the form of base, or of a pharmaceutically acceptable acid-addition salt, hydrate or solvate, for the preparation of a medicament for treating the pathologies mentioned above forms an integral part of the invention.

Another subject of the invention is medicaments comprising a compound of formula (I), or an acid-addition salt, or else a pharmaceutically acceptable hydrate or solvate of the compound of formula (I). The therapeutic use of these medicaments is especially in the treatment of the pathologies mentioned above.

According to another of its aspects, the present invention relates to pharmaceutical compositions containing, as active principal, at least one compound according to the invention. These pharmaceutical compounds contain an effective dose of a compound according to the invention, or a pharmaceutically acceptable acid-addition salt, hydrate or solvate of said compound, and optionally one or more pharmaceutically acceptable excipients.

Said excipients are chosen, according to the pharmaceutical form and the desired administration form, from the usual excipients known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principal of formula (I) above, or the possible acid-addition salt, solvate or hydrate thereof, may be administered in a unit administration form, as a mixture with standard pharmaceutical excipients, to animals and humans for the prophylaxis or treatment of the above disorders or diseases.

The appropriate unit administration forms comprise oral forms such as tablets, soft or hard gel capsules, powders, granules, chewing gums and oral solutions or suspensions, sublingual, buccal, intratracheal, intraocular and intranasal administration forms, forms for administration by inhalation, subcutaneous, intramuscular or intravenous administration forms and rectal or vaginal administration forms. For topical application, the compounds according to the invention may be used in creams, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropyl methyl cellulose | 2.25 mg |
| Magnesium stearate | 3.0 mg |

Said unit forms are dosed to allow a daily administration of from 0.01 to 20 mg of active principal per kg of body weight, depending on the presentation form.

There may be particular cases in which higher or lower doses are suitable, and such doses also form part of the invention. According to the usual practice, the dose that is suitable for each patient is determined by the doctor according to the mode of administration and the weight and response of said patient.

According to another of its aspects, the invention also relates to a method for treating the pathologies mentioned above, which comprises the administration of an effective dose of a compound according to the invention, a pharmaceutically acceptable acid-addition salt thereof or a solvate or hydrate of said compound.

The invention claimed is:

1. A compound corresponding to formula (I):

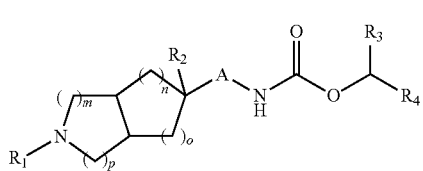

in which
$R_2$ represents a hydrogen or fluorine atom or a hydroxyl, cyano, trifluoromethyl, $C_{1-6}$-alkyl, $C_{1-6}$-alkoxy or $NR_8R_9$ group;
m and p have the value 1;
n and o have the same value and have the value 0 or 1;
A represents a covalent bond or a group $C_{1-8}$-alkylene;
$R_1$ represents a group $R_5$ optionally substituted with one or more groups $R_6$ and/or $R_7$;
$R_5$ represents a group chosen from phenyl, pyridyl, pyridazinyl, pyrimidinyl, pyrazinyl, triazinyl, naphthalenyl, quinolinyl, isoquinolinyl, phthalazinyl, quinazolinyl, quinoxalinyl, cinnolinyl and naphthyridinyl;
$R_6$ represents a halogen atom or a cyano, —$CH_2CN$, nitro, hydroxyl, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O-group;
$R_7$ represents a group chosen from furyl, pyrrolyl, thienyl, oxazolyl, isoxazolyl, thiazolyl, isothiazolyl, imidazolyl, pyrazolyl, phenyl, pyridyl, pyridazinyl, pyrimidinyl, pyrazinyl and triazinyl; the group(s) $R_7$ possibly being substituted with one or more groups $R_6$ that may be identical to or different from each other;
$R_3$ represents a hydrogen or fluorine atom, a group $C_{1-6}$-alkyl or a trifluoromethyl group;
$R_4$ represents a 5-membered heterocycle chosen from furyl, pyrrolyl, thienyl, thiazolyl, isothiazolyl, oxazolyl, isoxazolyl, pyrazolyl, oxadiazolyl, thiadiazolyl, imidazole, triazolyl and tetrazolyl;
this heterocycle being optionally substituted with one or more substituents chosen from a halogen atom, a $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)(C_{1-3}$-alkylene-$NR_{10}R_{11})$, $SO_2R_8$, $SO_2NR_8R_9$ or —O—($C_{1-3}$-alkylene)-O-group;
$R_8$ and $R_9$ represent, independently of each other, a hydrogen atom or a $C_{1-6}$-alkyl group, or form, with the atom(s) that bear(s) them,
in the case of $NR_8R_9$, a ring chosen from azetidine, pyrrolidine, piperidine, morpholine, thiomorpholine, azepine, oxazepine and piperazine rings, this ring being optionally substituted with a $C_{1-6}$-alkyl or benzyl group;
in the case of $NR_8COR_9$, a lactam ring; in the case of $NR_8CO_2R_9$, an oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring;
$R_{10}$ and $R_{11}$ represent, independently of each other, a hydrogen atom or a $C_{1-6}$-alkyl group; in the form of base or of acid-addition salt.

2. The compound of wherein $R_2$ represents a hydrogen atom or a fluorine atom; in the form of base or of acid-addition salt.

3. The compound of claim 1 wherein m, n, o and p have the value 1; in the form of base or of acid-addition salt.

4. The compound of claim 1, wherein A represents a covalent bond, a methylene or an ethylene; in the form of base or of acid-addition salt.

5. The compound of claim 1, wherein $R_1$ represents a group $R_5$ which is unsubstituted or is substituted with one or more groups $R_6$ and/or $R_7$;
$R_5$ represents a pyridyl or quinolinyl group;
$R_6$ represents a halogen atom, more particularly a fluorine or bromine atom, or a $C_{1-6}$-haloalkyl group, more particularly a trifluoromethyl group or a $C_{1-6}$-alkyl group, more particularly a methyl group;
$R_7$ represents a group chosen from pyrazolyl, pyridyl and phenyl, the latter groups possibly being substituted with one or more groups $R_6$ that may be identical to or different from each other; in the form of base or of acid-addition salt.

6. The compound of claim 1, wherein $R_3$ represents a hydrogen atom; in the form of base or of acid-addition salt.

7. The compound of claim 1, wherein $R_4$ represents a group chosen from a thiazolyl, a triazolyl or an isoxazolyl; this group being unsubstituted or substituted with one or more $C_{1-6}$-alkyl, $CO_2R_8$ or $CONR_8R_9$ groups; $R_8$ and $R_9$ represent, independently of each other, a hydrogen atom or a $C_{1-6}$-alkyl group; in the form of base or of acid-addition salt.

8. The compound of claim 1 chosen from:
thiazol-4-ylmethyl ({(3aR,5s,6aS)-2-[6-(trifluoromethyl)pyrid-2-yl]octahydrocyclopenta[c]pyrrol-5-yl}methyl)carbamate (exo);
thiazol-4-ylmethyl {[(3aR,5s,6aS)-2-(5-bromopyrid-2-yl]octahydrocyclopenta[c]pyrrol-5-yl}methyl)carbamate (exo);
thiazol-4-ylmethyl ({(3aR,5s,6aS)-2-[5-(4-fluorophenyl)pyrid-2-yl]-octahydrocyclopenta[c]pyrrol-5-yl}methyl)carbamate (exo);
thiazol-4-ylmethyl ({(3aR,5s,6aS)-2-[5-(1-methyl-1H-pyrazol-4-yl)pyrid-2-yl]octahydrocyclopenta[c]pyrrol-5-yl}methyl)carbamate (exo);
thiazol-4-ylmethyl {(3aR,5s,6aS)-2-[6-(trifluoromethyl)pyrid-2-yl]octahydrocyclopenta[c]pyrrol-5-yl}carbamate (exo);
thiazol-4-ylmethyl [(3aR,5s,6aS)-2-(6-fluoroquinolin-2-yl)octahydrocyclopenta[c]pyrrol-5-yl]carbamate (exo);
(1-methyl-1H-1,2,4-triazol-5-yl)methyl ({(3aR,5s,6aS)-2-[5-(4-fluorophenyl)pyrid-2-yl]octahydrocyclopenta[c]pyrrol-5-yl}methyl)carbamate (exo);
(1-methyl-1H-1,2,4-triazol-5-yl)methyl {[(3aR,5s,6aS)-2-(5'-fluoro-2,3'-bipyrid-6-yl)octahydrocyclopenta[c]pyrrol-5-yl]methyl}carbamate (exo);
(3-carbamoylisoxazol-5-yl)methyl ({(3aR,5s,6aS)-2-[5-(4-fluorophenyl)pyrid-2-yl]octahydrocyclopenta[c]pyrrol-5-yl}methyl)carbamate (exo);

[3-(methylcarbamoyl)isoxazol-5-yl]methyl {2-[(3aR,5r,6aS)-2-(5-bromopyrid-2-yl)octahydrocyclopenta[c]pyrrol-5-yl]ethyl}carbamate (endo);

(3-carbamoylisoxazol-5-yl)methyl {2-[(3aR,5r,6aS)-2-(5-bromopyrid-2-yl)octahydrocyclopenta[c]pyrrol-5-yl]ethyl}carbamate (endo);

(3-carbamoylisoxazol-5-yl)methyl {[(3aR,5r,6aS)-5-fluoro-2-(6-fluoroquinolin-2-yl)octahydrocyclopenta[c]pyrrol-5-yl]methyl}carbamate (exo);

[3-(methylcarbamoyl)isoxazol-5-yl]methyl {[(3aR,5s,6aS)-2-(6-fluoroquinolin-2-yl)octahydrocyclopenta[c]pyrrol-5-yl]methyl}carbamate (exo);

[3-(methylcarbamoyl)isoxazol-5-yl]methyl [3-(6-fluoroquinolin-2-yl)-3-azabicyclo[3.1.0]hex-6-yl]carbamate;

ethyl 5-{[({3-[5-(4-fluorophenyl)pyrid-2-yl]-3-azabicyclo[3.1.0]hex-6-yl}carbamoyl)oxy]methyl}isoxazole-3-carboxylate;

(3-carbamoylisoxazol-5-yl)methyl [3-(6-fluoroquinolin-2-yl)-3-azabicyclo[3.1.0]hex-6-yl]carbamate;

(3-carbamoylisoxazol-5-yl)methyl {3-[5-(4-fluorophenyl)pyrid-2-yl]-3-azabicyclo[3.1.0]hex-6-yl}carbamate;

[3-(methylcarbamoyl)isoxazol-5-yl]methyl {3-[5-(4-fluorophenyl)pyrid-2-yl]-3-azabicyclo [3.1.0]hex-6-yl}carbamate;

[3-(dimethylcarbamoyl)isoxazol-5-yl]methyl {3-[5-(4-fluorophenyl)pyrid-2-yl]-3-azabicyclo[3.1.0]hex-6-yl}carbamate.

9. A process for preparing the compound of claim 1, comprising the step that consists in reacting an amine of general formula (II):

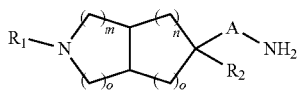

in which A, $R_1$, $R_2$, m, n, o and p are as defined in the general formula (I) according to claim 1, with a carbonate of general formula (III):

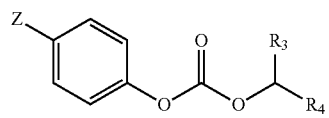

in which Z represents a hydrogen atom or a nitro group, and $R_3$ and $R_4$ are as defined in the general formula (I) according to claim 1, in the presence of a base, in a solvent at a temperature between room temperature and the reflux temperature of the solvent.

10. A process for preparing the compound of claim 1, comprising the step that consists in reacting a compound of general formula (IV):

in which A, $R_1$, $R_2$, m, n, o and p are as defined in the general formula (I) according to claim 1,

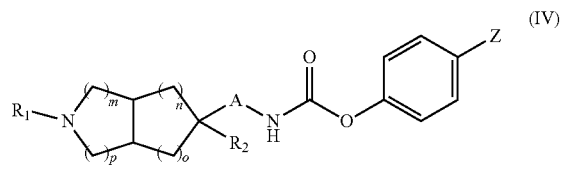

and Z represents a hydrogen atom or a nitro group, with an alcohol of general formula $HOCHR_3R_4$ (IIIa), in which $R_3$ and $R_4$ are as defined in the general formula (I) according to claim 1, in the presence of a base, in a solvent at a temperature between room temperature and the reflux temperature of the solvent.

11. A process for preparing the compound of claim 1, comprising the step that consists in reacting a compound of general formula (Ia):

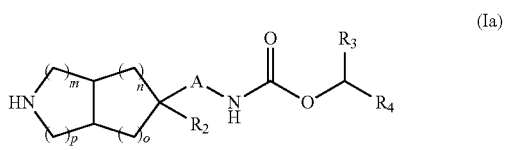

in which A, $R_2$, $R_3$, $R_4$, m, n, o and p are as defined in the general formula (I) according to claim 1, with a derivative of formula $R_1$-$U_1$ (V), in which $R_1$ is as defined in the general formula (I) according to claim 1 and $U_1$ represents a halogen atom or a triflate group, using aromatic or heteroaromatic nucleophilic substitution reaction conditions or using Buchwald N-arylation or N-heteroarylation conditions.

12. A process for preparing the compound of claim 1, in which $R_1$ represents a group $R_5$ substituted especially with a group $R_6$ of the $C_{1-6}$-alkyl, $C_{3-7}$-cycloalkyl or $C_{3-7}$-cycloalkyl-$C_{1-3}$-alkylene type, or with a group $R_7$ as defined in the general formula (I) according to claim 1, comprising the step that consists in performing a coupling reaction, catalysed by means of a transition metal, on the compound of general formula (Ib):

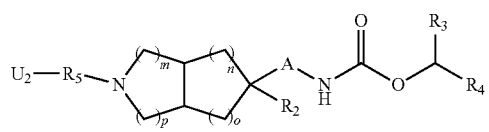

in which A, $R_2$, $R_3$, $R_4$, $R_5$, m, n, o and p are as defined in the general formula (I) according to claim 1 and $U_2$ represents a chlorine, bromine or iodine atom or a triflate group, $U_2$ being in the position in which it is desired to introduce the group $R_6$ or $R_7$:

either via a reaction of Suzuki type, for example using an alkyl, cycloalkyl, aryl or heteroaryl boronic acid;

or according to a reaction of Stille type, for example using an aryl or heteroaryl trialkylstannous derivative;

or via a reaction of Negishi type, for example using an alkyl, cycloalkyl, aryl or heteroaryl halide zincate derivative.

13. A pharmaceutical composition comprising the compound of claim 1, in the form of base or of a pharmaceutically acceptable acid-addition salt.

14. The pharmaceutical composition according to claim 13, further comprising one or more pharmaceutically acceptable excipients.

15. A method of treating acute or chronic pain of neurogenic type, acute or chronic pain associated with inflammatory diseases, acute or chronic peripheral pain, vertigo, vomiting, nausea, eating disorders, epilepsy, sleep disorders, renal ischaemia, cancers, inflammatory diseases, osteoporosis, gastrointestinal diseases, urinary incontinence or inflammation of the bladder in a patient in need thereof comprising administering to said patient a therapeutically effective amount of the pharmaceutical composition of claim 13.

* * * * *

UNITED STATES PATENT AND TRADEMARK OFFICE
CERTIFICATE OF CORRECTION

| | | |
|---|---|---|
| PATENT NO. | : 8,865,738 B2 | Page 1 of 1 |
| APPLICATION NO. | : 13/319635 | |
| DATED | : October 21, 2014 | |
| INVENTOR(S) | : Ahmed Abouabdellah et al. | |

It is certified that error appears in the above-identified patent and that said Letters Patent is hereby corrected as shown below:

In the Claims:

At column 31, claim number 1, line number 34: please replace "$C_{3-7}$-cycloalkyl-$C_{1-3}$-alkylene, $NR_8R_9$," with --$C_{3-7}$-cycloalkyl-$C_{1-3}$-alkylene, $C_{3-7}$-cycloalkyl-$C_{1-3}$-alkylene-O-, $NR_8R_9$,--;

At column 31, claim number 1, line number 36: please replace "$COR_5$" with --$COR_8$--;

At column 31, claim number 1, line number 37: please replace "—O—($C_{1-3}$-alkylene)-O-group" with -- -O-($C_{1-3}$-alkylene)-O- group--;

At column 31, claim number 1, line numbers 57-58: please replace "—O—($C_{1-3}$-alkylene)-O-group" with -- -O-($C_{1-3}$-alkylene)-O- group--;

At column 32, claim number 2, line number 7: please replace "The compound of wherein $R_2$" with --The compound of claim 1, wherein $R_2$--;

At column 32, claim number 8, line numbers 43-44: please replace "thiazol-4-ylmethyl {[(3aR,5s,6aS)-2-(5-bromopyrid-2-yl]octahydrocyclopenta[c]pyrrol-5-yl}methyl)carbamate" with --thiazol-4-ylmethyl{[(3aR,5s,6aS)-2-(5-bromopyrid-2-yl)octahydrocyclopenta[c]pyrrol-5-yl]methyl}carbamate--;

At column 32, claim number 8, line numbers 46-48: please replace "thiazol-4-ylmethyl ({(3aR,5s,6aS)-2-[5-(4-fluorophenyl)pyrid-2-yl]-octahydrocyclopenta[c]pyrol-5-yl}methyl)carbamate" with --thiazol-4-ylmethyl({ (3aR,5s,6aS)-2-[5-(4-fluorophenyl)pyrid-2-yl]-octahydrocyclopenta[c]pyrrol-5-yl}methyl)carbamate--;

At column 33, claim number 8, line numbers 27-29: please replace "[3-(methylcarbamoyl)isoxazol-5-yl]methyl {3-[5-(4-fluorophenyl)pyrid-2-yl]-3-azabicyclo[3.1.0]hex-6-yl}carbamate;" with --[3-(methylcarbamoyl)isoxazol-5-yl]methyl{3-[5-(4-fluorophenyl)pyrid-2-yl]-3-azabicyclo[3.1.0]hex-6-yl}carbamate;--.

Signed and Sealed this
Twentieth Day of October, 2015

Michelle K. Lee
*Director of the United States Patent and Trademark Office*